(12) United States Patent
Krackhardt et al.

(10) Patent No.: US 8,217,009 B2
(45) Date of Patent: Jul. 10, 2012

(54) ALLORESTRICTED PEPTIDE-SPECIFIC T CELLS

(75) Inventors: Angela Krackhardt, Munich (DE); Ingrid Schuster, Munich (DE); Dirk Busch, Munich (DE)

(73) Assignee: Helmholtz Zentrum Munchen Deutsches Forschungszentrum fur Gesundheit und Umwelt, Neuherberg (DE)

( * ) Notice: Subject to any disclaimer, the term of this patent is extended or adjusted under 35 U.S.C. 154(b) by 231 days.

(21) Appl. No.: 12/304,918

(22) PCT Filed: Jun. 18, 2007

(86) PCT No.: PCT/EP2007/056029
§ 371 (c)(1),
(2), (4) Date: Oct. 23, 2009

(87) PCT Pub. No.: WO2007/147806
PCT Pub. Date: Dec. 27, 2007

(65) Prior Publication Data
US 2010/0055117 A1 Mar. 4, 2010

(30) Foreign Application Priority Data
Jun. 20, 2006 (EP) ..................................... 06012680

(51) Int. Cl.
*A61K 38/00* (2006.01)
(52) U.S. Cl. ..................................... 514/19.3
(58) Field of Classification Search .................. None
See application file for complete search history.

(56) References Cited

U.S. PATENT DOCUMENTS
2006/0051772 A1* 3/2006 Valmori et al. .................. 435/6

FOREIGN PATENT DOCUMENTS
WO    WO 2004050705 A2 *  6/2004
WO    WO2007/147806       12/2007

OTHER PUBLICATIONS

Chen et al., Identification of human tumor antigens by serological expression cloning: an online review on SEREX. Cancer Immun 2004 [updated Mar 10, 2004; cited Apr. 1, 2004]. URL: http://www.cancerimmunity.org/SEREX/.*
Reche et al., Hum Immunol. Sep. 2002;63(9):701-9.*
Hughes et al., Hum Gene Ther. Apr. 2005; 16(4):457-72.*
Schuster et al., Blood, Oct. 15, 2007, vol. 110, No. 8, pp. 2931-2939.*
Janeway et al., Immunobiology, 5th Ed., Garland Science, pp. 106-108 and 260-263, (2001).*
Garcia et al., Cell, vol. 122, 333-336, Aug. 12, 2005.*
Khouri et al., "Nonablative allogeneic stem-cell transplantation for advanced/recurrent mantle-cell lymphoma," J. Clin. Oncol., vol. 21, No. 23, pp. 4407-4412 (2003).

Marks et al., "The toxicity and efficacy of donor lymphocyte infusions given after reduced-intensity conditioning allogeneic stem cell transplantation," Blood, vol. 100, No. 9, pp. 3108-3114 (2002).
Rai et al., "Alemtuzumab in previously treated chronic lymphocytic leukemia patients who also had received fludarabine," J. Clin. Oncol., vol. 20, No. 18, pp. 3891-3897 (2002).
Sadovnikova et al., "Peptide-specific cytotoxic T lymphocytes restricted by nonself major histocompatibility complex class I molecules: reagents for tumor immunotherapy," PNAS, vol. 93, No. 23, pp. 13114-13118 (1996).
Schetelig et al., "Evidence of a graft-versus-leukemia effect in chronic lymphocytic leukemia after reduced-intensity conditioning and allogeneic stem cell transplantation: the Cooperative German Transplant Study Group," J. Clin. Oncol., vol. 21, No. 14, pp. 2747-2753 (2003).
Yee et al., "Isolation of high avidity melanoma-reactive CTL from heterogenous populations using peptide-MHC tetramers," J. Immunol., vol. 162, No. 4, pp. 2227-2234 (1999).
International Search Report and Written Opinion of the International Searching Authority corresponding to International Application No. PCT/EP2007/056029 dated Oct. 15, 2007.
Krackhardt et al., Identification of tumor-associated antigens in chronic lymphocytic leukemia by SEREX. *Blood.* vol. 100, No. 6 pp. 2123-2131 (2002).
Krackhardt et al., T-cell responses against chronic lymphocytic leukemia cells: implications for immunotherapy. *Blood.* vol. 100, No. 1 pp. 167-173 (2002).
Mayr et al., Transduction of CLL cells by CD40 ligand enhances an antigen-specific immune recognition by autologous T cells. *Blood.* vol. 106, No. 9 pp. 3223-3226 (2005).
Weekes et al., The memory cytotoxic T-lymphocyte (CTL) response to human cytomegalovirus infection contains individual peptide-specific CTL clones that have undergone extensive expansion in vivo. *Journal of Virology.* vol. 73, No. 3 pp. 2099-2108 (1999).
Yayoshi-Yamamoto et al., FRL, a novel formin-related protein, binds to Rac and regulates cell motility and survival of macrophages. *Molecular and Cellular Biology.* vol. 20, No. 18 pp. 6872-6881 (2000).
Katoh et al., Identification and characterization of human FMNL1, FMNL2 and FMNL3 genes in silico. *International Journal of Oncology.* vol. 22, No. 5 pp. 1161-1168 (2003).
Katoh et al., Identification and characterization of human GRID2IP gene and rad Grid2ip gene in silico. *International Journal of Molecular Medicine.* vol. 12, No. 6 pp. 1015-1019 (2003).
Santamaria et al., Amino acid sequences of seven V beta, eight V alpha, and thirteen J alpha novel human TCR genes. *Immunogenetics.* vol. 38, No. 2 p. 163 (1993).

(Continued)

Primary Examiner — Zachary Skelding
(74) Attorney, Agent, or Firm — Jenkins, Wilson, Taylor & Hunt, P.A.

(57) ABSTRACT

The present invention is directed to a T cell receptor (TCR) recognizing antigenic peptides derived from tumor-associated antigen FMNL1/KW13 and being capable of inducing peptide specific killing of a target cell. The present invention is further directed to one antigenic peptides derived from tumor-associated antigen FMNL1/KW13, to an antigen specific T cell, comprising said TCR, to a nucleic acid coding for said TCR and to the use of the antigen specific T cells for the manufacture of a medicament for the treatment of malignancies characterized by overexpression of FMNL1/KW13.

1 Claim, 16 Drawing Sheets

OTHER PUBLICATIONS

Larsen et al., "An integrative approach to CTL epitope prediction: a combined algorithm integrating MHC class I binding, TAP transport efficiency, and proteasomal cleavage predictions," Eur. J. Immunol., vol. 35, No. 8, pp. 2295-2303 (2005).

Parker et al., "Scheme for ranking potential HLA-A2 binding peptides based on independent binding of individual peptide side-chains," J. Immunol., vol. 152, No. 1, pp. 163-175 (1994).

* cited by examiner

```
MGNAAGSAEQ PAGPAAPPPK QPAPPKQPMP AAGELEERFR RALNCHRLPP DKVQLLSQYD    60
NEKKWELICD QERFQVKNPP AAYIQKLKSY VDTGGVSRKV AADWMSNLGF KPRVQESTQV   120
LRELETSLRF NHIGWVQEFL NEENRGLDVL LEYLAFAQCS VTYDMESTDN GASNSEKNKP   180
LEQSVEDLSK GPPSSVPKSR HLTIKLTPAH SRKALRNSRI VSQKDDVHVC IMCLRAIMNY   240
QSGFSLVMNH PACVNEIALS LNNKNPRTKA LVLELLAAVC LVRGGHDIIL AAFDNFKEVC   300
GEQHRFEKLH EYFRNEDSNI DFMVACMQFI NIVVHSVENM NFRVFLQYEF THLGLDLYLE   360
RLRLTESDKL QVQIQAYLDN IFDVGALLED TETKNAVLEH MEELQEQVAL LTERLRDAEN   420
ESMAKIAELE KQLSQARKEL ETLRERFSES TAMGASRRPP EPEKAPPAAP TRPSALELKV   480
EELEEKGLIR ILRGPGDAVS IEJLPVAVAT PSGGDAPTPG VPTGSPSPDL APAAEPAPGA   540
APPPPPPLPG LPSPQEAPPS APPQAPPLPG SPEPPPAPPL PGDLPPPPPP PPPPPGTDGP   600
VPPPPPPPPP PPGGPPDALG RRDSELGPGV KAKKPIQTKF RMPLLNWVAL KPSQTTGTVF   660
TELNDEKVLQ ELDMSDFEEQ FKTKSQGPSL DLSALKSKAA QKAPSKATLI EAHRAKNLAI   720
TLRKGNLGAE RICQAIEAYD LQALGLDFLE LLMRFLPTEY ERSLITRFER EQRPMEELSE   780
EDRFMLCFSR IPRLPERMTT LTFLGNFPDT AQLLMPQLNA IIAASMSIKS SDKLRQILEI   840
VLAFGNYMNS SKRGAAYGFR LQSLDALLEM KSTDRKQTLL HYLVKVIAEK YPQLTGFHSD   900
LHFLDKAGSV SLDSVLADVR SLQRGLELTQ REFVRQDDCM VLKEFLRANS PTHDKLLADS   960
KTAQEAFESV VEYFGENPKT TSPGLFFSLF SRFIKAYKKA EQEVEQWKKE AAAQEAGADT  1020
PGKGEPPAPK SPPKARRPQM DLISELKRRQ QKEPLIYESD RDGAISDIIT VIKTVPFTAR  1080
TGKRTSRLLC EASLGEEMPL                                             1100
```

B

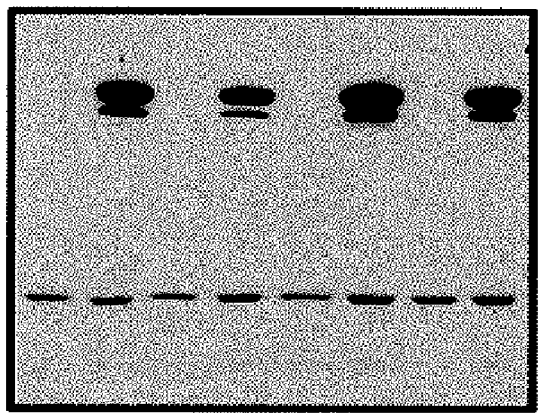

ALLORESTRICTED PEPTIDE-SPECIFIC T CELLS

CROSS-REFERENCE TO RELATED APPLICATION

The instant application is a National Stage Application filed under 35 U.S.C. §371 of PCT International Patent Application No. PCT/EP2007/056029, filed Jun. 18, 2007. The disclosure of PCT International Patent Application No. PCT/EP2007/056029 is hereby incorporated by reference in its entirety.

The present invention is directed to T cell receptors (TCR) recognizing antigenic peptides derived from tumor-associated antigen FMNL1/KW13 or the murine homolog FRL and being capable of inducing peptide specific killing of a target cell. The present invention is further directed to antigenic peptides derived from tumor-associated antigen FMNL1/KW13, to an antigen specific T cell, comprising said TCR, to a nucleic acid coding for said TCR and to the use of the antigen specific T cells for the manufacture of a medicament for the treatment of malignancies characterized by overexpression of FMNL1/KW13. The present invention is further disclosing a method of generating antigen specific allorestrictive T cells.

BACKGROUND OF THE INVENTION

The present invention concerns the field of immunotherapies in B cell neoplasms, in particular B cell lymphoma, including acute and chronic lymphocytic leukemias.

The incidence of B cell neoplasms is increasing, especially in Western Countries (NCI, SEER). Most cases of low grade lymphoma are diagnosed at advanced stages where no curative standard therapy is available. In chronic lymphocytic leukemia (CLL), there is still no established curative therapy available at any time point of diagnosis. In contrast, patients with high grade lymphoma or acute lymphoblastic leukemia benefit from intensive and potentially curative chemotherapy regimens. However, longterm prognosis is unfavourable for adult patients with recurrent disease. Thus, novel therapies are needed.

Immunotherapy has been shown to be highly successful in low grade lymphoma including CLL. There are target specific therapies using monoclonal antibodies which are directed against surface antigens as CD20 (Rituximab) and CD52 (Alemtuzumab) (1,2). However, tumor escape occurs due to down regulation of the target antigen from the cell surface. T cells are able to recognize peptides associated to MHC molecules derived from extra- and intracellular antigens. T cells are currently applied associated to allogeneic stem cell transplantation and responsible for a Graft versus leukemia effect (GvL effect) which has been shown to be present in different B cell neoplasms (3-5). However, one major disadvantage of this approach is Graft versus host disease (GvHD) due to transferred T cells unspecifically recognizing allogeneic MHC molecules. Using allorestricted peptide-specific T cells it might be possible to circumvent central tolerance against tumor associated self peptides and simultaneously dissociate beneficial graft versus leukemia effect from detrimental graft versus host disease (6,7).

Krackhardt et al., "Identification of tumor associated antigens in chronic lymphocytic leukaemia by SEREX", Blood September 2002, vol. 100, no. 6, pages 2123-2131, describe the identification of KW13/FMNL1. Here, peptide-specific autologous T cells were generated recognizing one single FMNL1-derived peptide (TLLHYLVKV; SEQ ID NO: 21). However, it turned out that these T cells did not recognize tumor cells as described in the paper. Thus, it is likely that the specific peptide is not an epitope presented on the surface of CLL cells. Moreover, the specific peptide has not been listed. In addition, no specific TCR has been described.

The identification of an antigenic epitope, however is of fundamental importance to use a specific antigen as target for a therapeutic approach as tumor cells can be only targeted if the specific peptide is presented on the surface of a cell. Given a protein length of 1100 amino acids, there are 1091 different nona-peptides which can be used for pulsing and most of them may not bind to the restriction element and/or are not produced by the immune proteasome, thus they are mostly not presented on the surface of a tumor cell.

Mayr et al., "Transduction of CLL cells by CD40 ligand enhances an antigen-specific immune recognition by autologous T cells", Blood November 2005, vol. 106, no. 9, compare the functional reactivity of T cell lines generated by stimulation with CD40L-AAV-transduced CLL cells, GFP-AAV-transduced CLL cells as well as native CLL cells and CLL cells stimulated by CD40-Ligand. Their read-out is an ELISPOT-assay where they use peptide-pulsed APC using different peptides for pulsing. They claim that they have generated antigen-specific T cells. However, several important controls are missing in order to prove the significance of the peptides used for detection of specific antigen recognition, as for example peptides and well characterized T cells for positive and negative controls, peptide dilution and tetramer-staining of T cell lines. As CD40L-activated CLL cells may prime for many antigens and peptide-pulsed CLL cells can express many other antigens, peptide-specificity is not shown in the manuscript. Moreover, no specific peptide is mentioned concerning KW13. The authors merely mention "KW13" in the methods section. KW13 is actually not a peptide but the whole FMNL1 protein. In addition, no specific TCR has been discovered and described. Thus regarding Mayr et al., no precise peptide has been described concerning KW13/FMNL1, no peptide-specificity has been proven, no epitope has been discovered, no specific TCR was shown. This is exactly the critical development which has been undertaken in our last work and which motivates us for the patent claims.

SUMMARY OF THE INVENTION

It one object of the present invention to generate allorestrictive T cells that bear TCR that have the capacity to recognize their MHC-peptide ligands on tumor cells. Furthermore, it is an object of the invention to provide a T cell based pharmaceutical composition that can be used for treating a patient suffering from lymphoma without a risk of graft-versus-host-disease (GVHD).

These objects are achieved by the subject-matter of the independent claims. Preferred embodiments are set forth in the dependent claims.

The inventors have generated allorestricted peptide-specific T cells with specificity against a defined peptide derived from the tumor associated antigen FMNL1/KW13. For example, it could be demonstrated (I) the identification of specific T cell receptor chains which are allo-HLA-A2 restricted and specific for our selected peptide RLPERMTTL (SEQ ID NO: 2) as well as the murine homolog RLPERMNTL (SEQ ID NO: 5) derived from the murine FMNL1 homologous protein and (II) that the selected peptide RLPERMTTL (SEQ ID NO: 2) derived from FMNL1/KW13 is a natural presented epitope overexpressed on malignant tissue shown by specific cytotoxicity against lymphoma cell lines, other malignant cell lines and primary tumor material of patients with chronic lymphocytic leukaemia and acute lymphoblastic leukemia. These T cells will be helpful for the development of immunotherapies against malignant lymphoma.

In healthy tissue, FMNL1/KW13 is almost exceptionally expressed in leukocytes. FMNL1/KW13-specific allorestricted T cells, therefore, are also useful in the development of immunotherapeutic strategies against rheumatoid diseases.

Using the present approach, allorestricted peptide-specific T cells with specificity against the selected peptides which also show specific cytotoxicity against malignant cell lines derived from lymphoma, renal cell carcinoma, melanoma, breast cancer, as well as cells from patients with chronic lymphocytic leukaemia, acute lymphoblastic leukaemia cells and also activated lymphocytes could be generated. In contrast, healthy tissue cell lines as fetal fibroblasts and fetal kidney cells were not recognized (FIGS. 4-12).

DETAILED DESCRIPTION OF THE INVENTION

According to a first aspect, the invention provides a T cell receptor (TCR) recognizing antigenic peptides derived from tumor-associated antigen FMNL1/KW13 or murine FRL and capable of inducing peptide specific killing of a target cell.

More precise information regarding tumor-associated antigen FMNL1/KW13 may be found in (8), including accession no., suggested function etc.

The term "TCR" as used in the present invention has the common meaning, which usually is attributed to that term in the pertinent field of technology. Thus, a rearranged T cell receptor (TCR) comprises a complex of two chains (α-chain and β-chain) containing a CDR3-region of rearranged TCR VDJ genes mainly involved in the recognition of antigenic determinants (epitopes) represented in the MHC context. More detailed information can be found in "*Immunobiology, the immune system in health and disease*", Charles A. Janeway, et al, 5 ed. 2001 and other standard literature.

An "antigenic peptide" as used herein is defined as comprising at least one antigenic determinant, i.e. an epitope. The latter is a part of a macromolecule that is being recognized by the immune system, in the present case specifically by cytotoxic T cells.

Accordingly, the TCR of the present invention specifically recognizes one of the epitopes of any of SEQ ID NO: 1-5 and/or peptides/proteins containing same. It is noted that the epitope according to SEQ ID NO: 2 turned out to be most preferred in the present invention since it is a natural presented epitope overexpressed on malignant tissue and the TCR recognizing same effectively induced a specific cytotoxicity against lymphoma cell lines. The present invention also provides an homologous peptide to epitope of SEQ ID NO: 2, i.e. the murine homologue derived from FRL.

It is noted that the invention is not restricted to the precise amino acid sequences as defined herein, but also include variants of the sequences, for example deletions, insertions and/or substitutions in the sequence, which cause for so-called "silent" changes.

Preferably, such amino acid substitutions are the result of substitutions which substitute one amino acid with a similar amino acid with similar structural and/or chemical properties, i.e. conservative amino acid substitutions.

Amino acid substitutions can be performed on the basis of similarity in polarity, charges, solubility, hydrophobic, hydrophilic, and/or amphipathic (amphiphil) nature of the involved residues. Examples for hydrophobic amino acids are alanine, leucine, isoleucine, valine, proline, phenylalanine, tryptophan and methionine. Polar, neutral amino acids include glycine, serine, threonine, cysteine, thyrosine, asparagine and glutamine. Positively (basic) charged amino acids include arginine, lysine and histidine. And negatively charged amino acids include aspartic acid and glutamic acid.

The allowed degree of variation can be experimentally determined via methodically applied insertions, deletions or substitutions of amino acids in a peptide and testing the resulting variants for their biological activity as an epitope. In case of variation of the TCR-CDR3 region specificity and function of the modified TCR can be experimentally investigated by TCR expression in transduced cells or by purified TCRs analyzed with surface plasmon resonance (e.g. Biacore).

An example of such a variant is the sequence of the murine homologue of SEQ ID NO: 2. Whereas the human sequence is RLPERMTTL (SEQ ID NO: 2), the murine homologue is RLPERMNTL (SEQ ID NO: 5). This variant showed also a very good recognition by TCR.

According to a further preferred embodiment, the TCR contains one or more of the amino acids of SEQ ID NO: 9-14.

In a second aspect, the present invention provides an antigenic peptide derived from tumor-associated antigen FMNL1/KW13 being selected from one of SEQ ID NO: 1-5.

However, also the epitopes of SEQ ID NO: 6-8 are contemplated herein.

According to a third aspect, the present invention provides an antigen specific T cell, comprising a TCR as defined above.

Said T cell preferably is a T cell with effector cell characteristics, more preferably a cytokine producing T cell, a cytotoxic T cell or regulatory T cell, preferably CD4+ or CD8+ T cells. Most preferably, the T cell is an autologous T cell.

In a fourth aspect, the invention provides a nucleic acid coding for a part of a TCR (CDR3-region) as defined above. Respective sequences are provided as SEQ ID NO: 15-20.

An additional aspect is directed to a vector, which comprises the nucleic acid coding for said TCR. This vector is preferably an expression vector which contains a nucleic acid according to the invention and one or more regulatory nucleic acid sequences. Preferably, this vector is a plasmid or a retroviral vector.

The invention further comprises a PBMC, which has been transformed with the vector as defined above. This can be done according to established methods such as those described in Engels et al., 2005 (9).

In a still further aspect, the present invention provides a pharmaceutical composition, which comprises the T cells or PBMCs as explained above and a pharmaceutically acceptable carrier.

Those active components of the present invention are preferably used in such a pharmaceutical composition in doses mixed with an acceptable carrier or carrier material, that the disease can be treated or at least alleviated. Such a composition can (in addition to the active component and the carrier) include filling material, salts, buffer, stabilizers, solubilizers and other materials, which are known state of the art.

The term "pharmaceutically acceptable" defines a non-toxic material, which does not interfere with effectiveness of the biological activity of the active component. The choice of the carrier is dependent on the application.

The pharmaceutical composition can contain additional components which enhance the activity of the active component or which supplement the treatment. Such additional components and/or factors can be part of the pharmaceutical composition to achieve synergistic effects or to minimize adverse or unwanted effects.

Techniques for the formulation or preparation and application/medication of active components of the present invention are published in "Remington's Pharmaceutical Sciences", Mack Publishing Co., Easton, Pa., latest edition. An appropriate application is a parenteral application, for example intramuscular, subcutaneous, intramedular injections as well as intrathecal, direct intraventricular, intravenous, intranodal, intraperitoneal or intratumoral injections. The intravenous injection is the preferred treatment of a patient.

According to a preferred embodiment, the pharmaceutical composition is an infusion or an injection or a vaccine.

According to a further aspect, the present invention is directed to the use of the antigen specific T cells or PBMCs as explained above for the manufacture of a medicament for the treatment of malignancies characterized by overexpression of FMNL1/KW13, preferably chronic lymphocytic leukemia (CLL), or rheumatoid diseases.

In a further aspect, the invention provides a method of generating antigen specific allorestrictive T cells comprising the steps of
a) providing a FMNL1/KW13 (or FRL) derived antigenic peptide as defined above;
b) pulsing antigen presenting cells (APCs) with said peptide;
c) priming peripheral blood lymphocytes (PBLs) with said APCs;
d) selecting those T cells which are specific for the resulting MHC-peptide ligand.

The APC's are preferably selected from dendritic cells, activated B cells, monocytes, macrophages, activated T cells, hematological malignancies with antigen presenting capacities and/or EBV-transformed lymphoblastoid cell lines.

Dendritic cells (DC) are in particular preferred. Mature dendritic cells (DCs) express both MHC class I and class II molecules at high levels, along with a wide variety of costimulatory molecules, which provide them with the full capacity to prime naïve T cells that have not encountered antigen previously. They also have all the necessary genes/proteins that allow them to process and present antigens form intracellular proteins in their MHC class I and class II molecules. Thus, they are optimal antigen presenting cells (APCs) to use as stimulating cells for induction of both CD4 and CD8 T cells responses.

The selection step d) is preferably performed by means of measuring the cytokine release of the T cells or other measures of T cell activation. For example, the activated T cells can be cloned as individual cells and following expansion, the T cell clones can be analyzed for their MHC-peptide specificity and those with the desired specificity can be selected for further use (10). Alternatively, soluble MHC-peptide ligands in various forms, such as tetramers, can be marked with a fluorescent label and incubated with the activated T cells. Those T cells bearing TCR that interact with the tetramers can then be detected by flow cytometry and sorted on the basis of their fluorescence (11). Furthermore, T cells can be stimulated for short periods of time with tumor cells to which they should react and their interferon gamma secretion detected by capture reagents, for example as published (12).

According to a preferred embodiment, the method of the invention further comprises the step of expanding the T cells selected in d) ex vivo. This can be done by co-culturing the selected T cells with APC generated in the same manner as used for their initial priming, adding new APC to the T cell cultures every 7-10 days and providing the cells with fresh culture medium on a regular basis that contains supplementary cytokines, dependent upon the type of T cell that one is expanding.

The present invention in the following is illustrated by the Figures and Examples presented below, which in no way should be construed to be limiting the scope of the invention.

BRIEF DESCRIPTION OF THE DRAWINGS

FIG. 13. Generation of the FMNL1-specific antibody. (A) Human FMNL1 sequence (Swiss-Prot database, Accession No. O95466; SEQ ID NO: 25). Matched peptides detected by mass spectrometry analysis are shown (bold and framed) covering 24% of the protein. (B) Four different monoclonal antibody supernatants (5C9, 5B12, 6F2, 5A1) were tested in a Western blot using 50 µg of cell lysates from T293 cells transfected with pCMV-FMNL1 (F) and pCMV-Vector alone (M).

Figure 15:
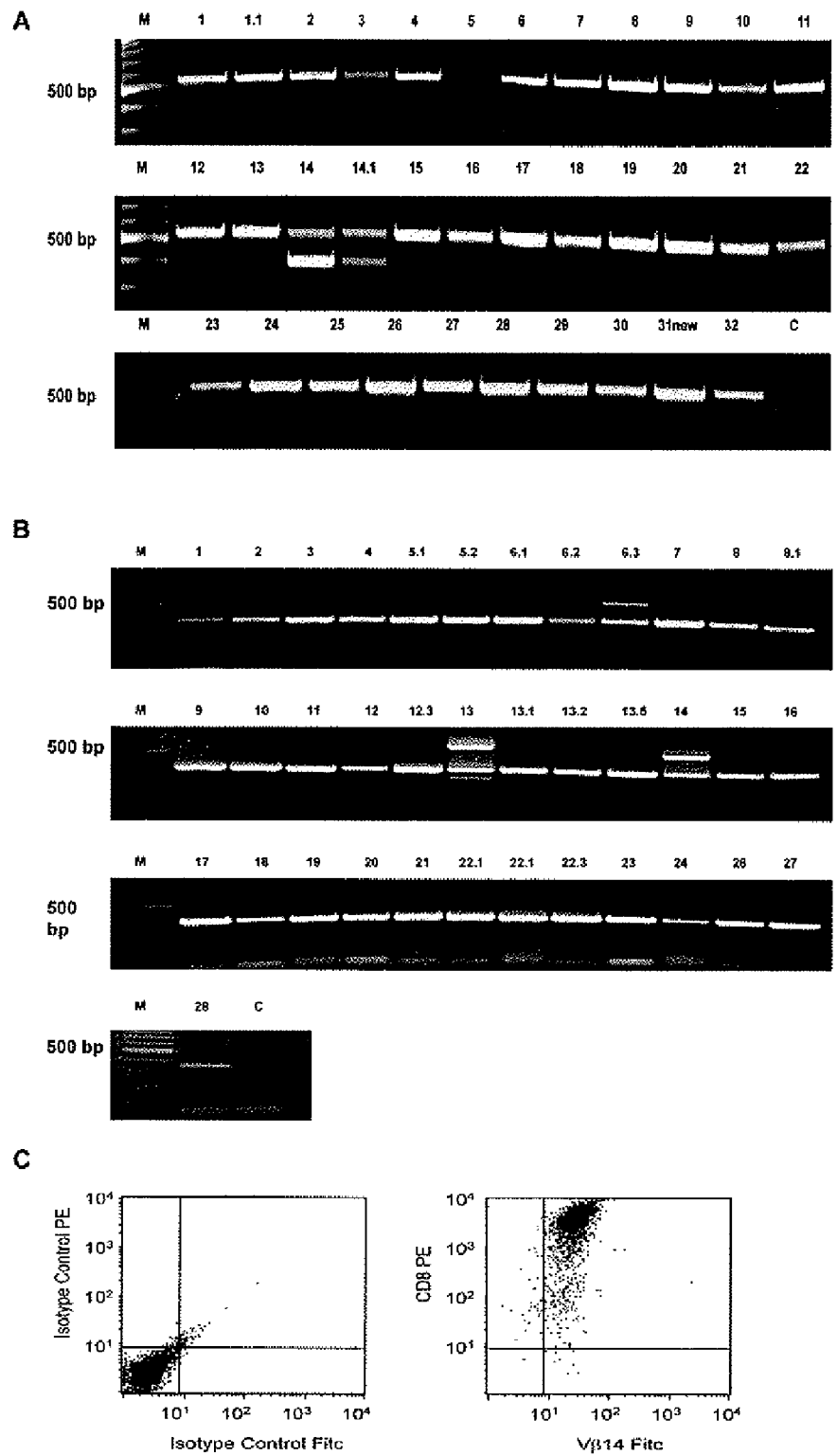

FIG. 15. TCR analysis of the FMNL1-PP2-specific T-cell clone SK22. (A) Analysis of the TCR α-chain repertoire of clone SK22 was performed using 34 single V alpha segment-specific primers. The primers Vα14 (band at 401 bp) and Vα14.1 (band at 459 bp) amplified identical in-frame CDR3-sequences. Control primers were used to amplify the constant chain (547 bp). Additional fuzzy bands did not result in any readable sequence. (B) TCR β-chain analysis was performed using 37 V beta segment-specific primers. The primers Vβ13 (bands at 278 and 632 bp) and Vβ14 (bands at 187 and 541 bp) resulted in identical in-frame CDR3-sequences. The primers for Vβ6.2 and Vβ6.3 (bands at 171 and 439 bp) resulted in amplified sequences with out-off-frame gene rearrangements. Additional fuzzy bands did not result in any readable sequence. Control primers were used to amplify the constant chain (351 bp). (C) The FMNL1-specific T-cell clone was stained with a FITC-conjugated anti-human Vβ14-specific antibody and a PE-conjugated anti-human CD8 antibody (right plot). The isotype control is shown in the left plot.

Figure 16:
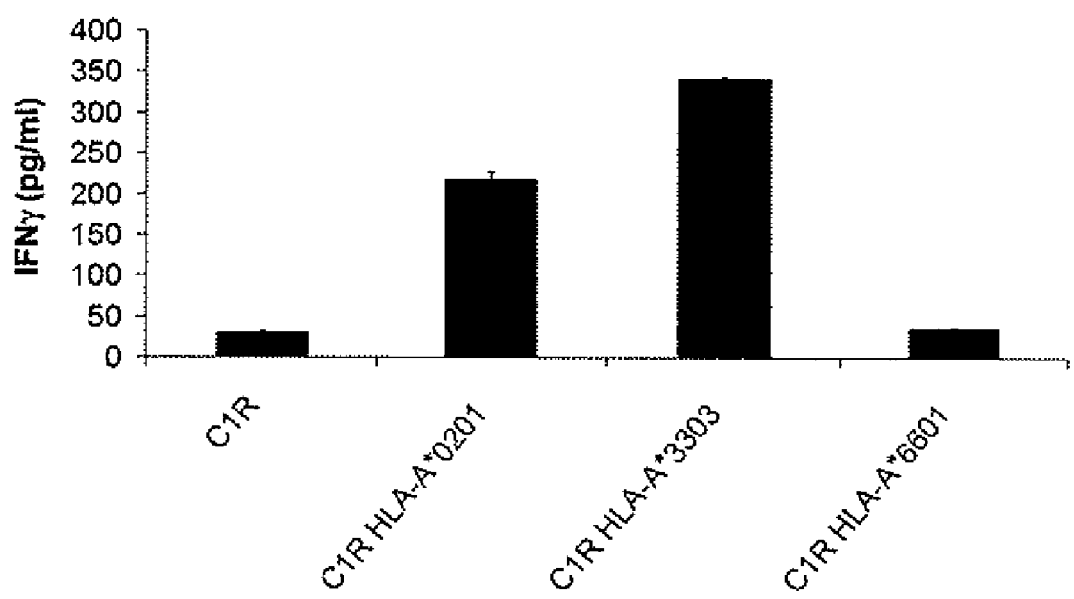

FIG. 16. Crossreactivity against HLA-A*3303. IFNγ-release was investigated by ELISA to test the FMNL1-PP2-specific T-cell clone against C1R cells transfected with HLA-A*3303 at effector:target ratio of 1:2. C1R cells transfected with HLA-A*0201 were used as positive control and untransfected C1R cells as well as C1R cells transfected with HLA*6601 as negative controls. Error bars indicate the standard deviation of tested duplicates. Results shown are representative for two experiments.

EXAMPLES

Antigen Selection

Figure 1:
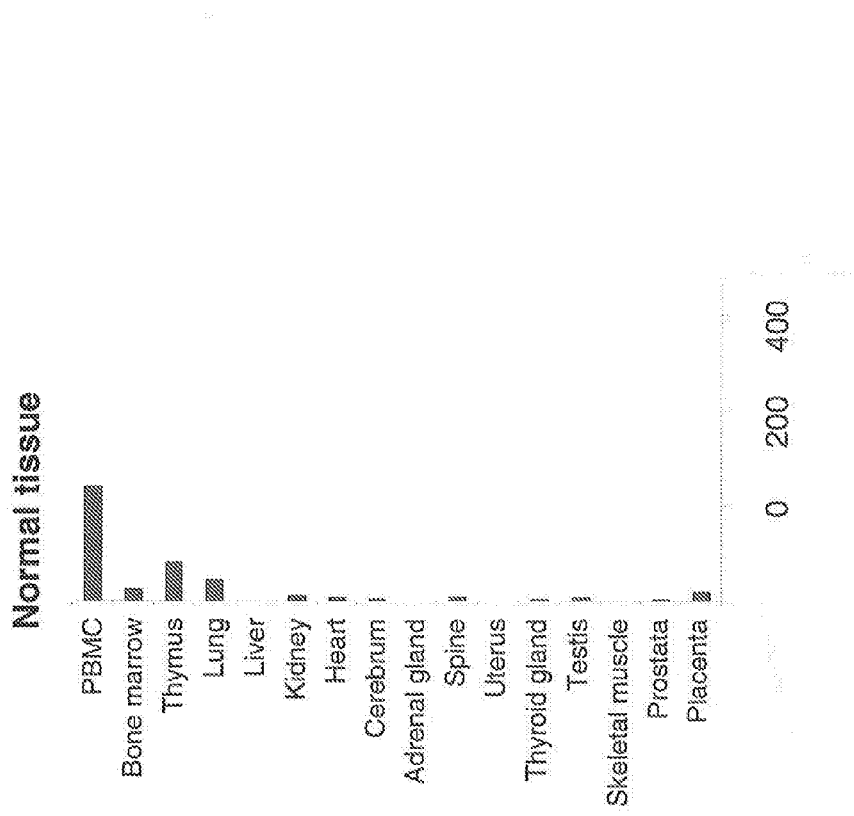
FIG. 1: Fold expression of FMNL1/KW13 mRNA in normal tissue compared to skeletal muscle investigated by quantitative RT-PCR.
Figure 2:
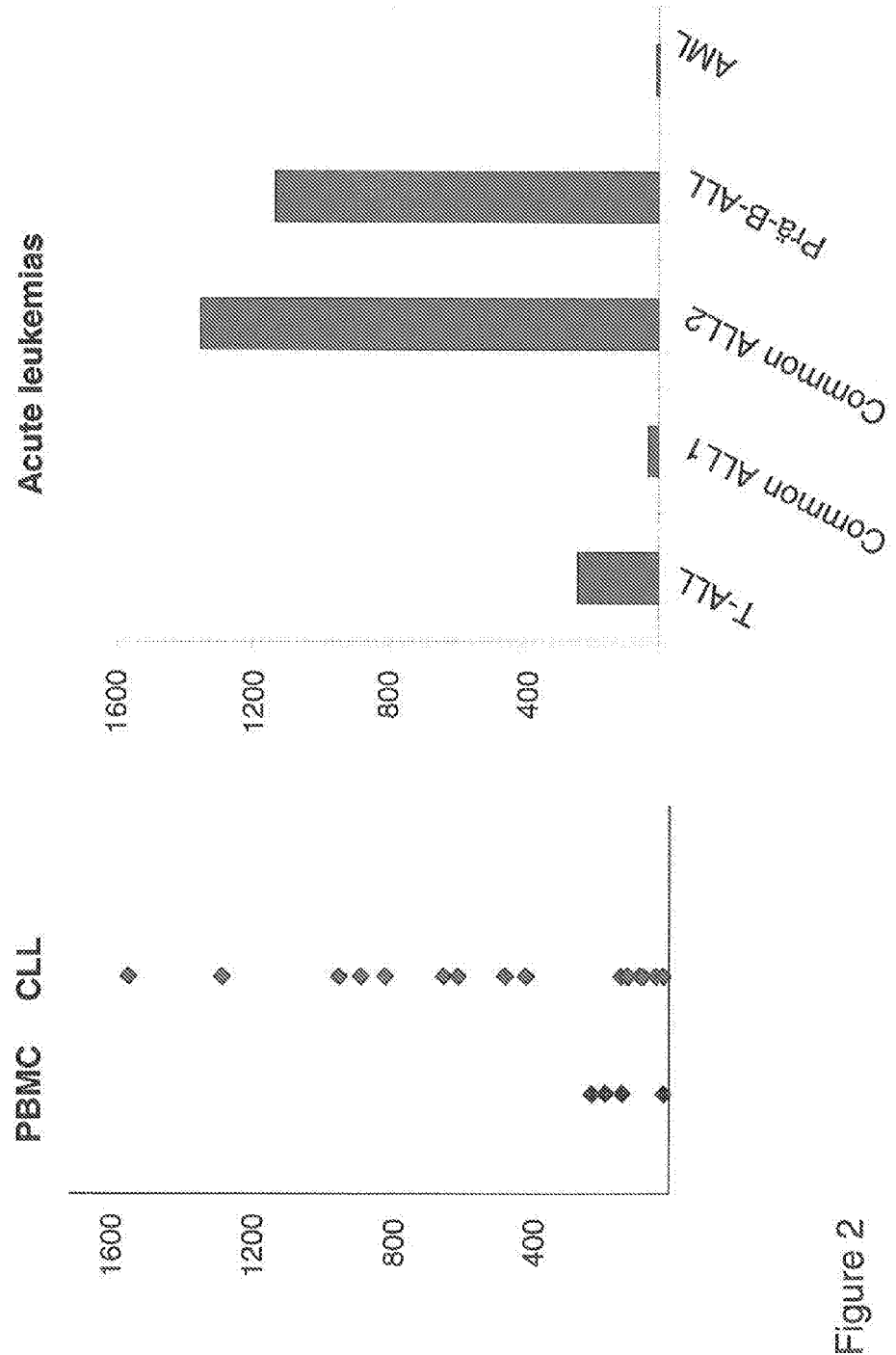
FIG. 2: Fold expression of FMNL1/KW13 mRNA in PBMC, native CLL samples and acute leukaemia samples compared to skeletal muscle investigated by quantitative RT-PCR.
Figure 3:
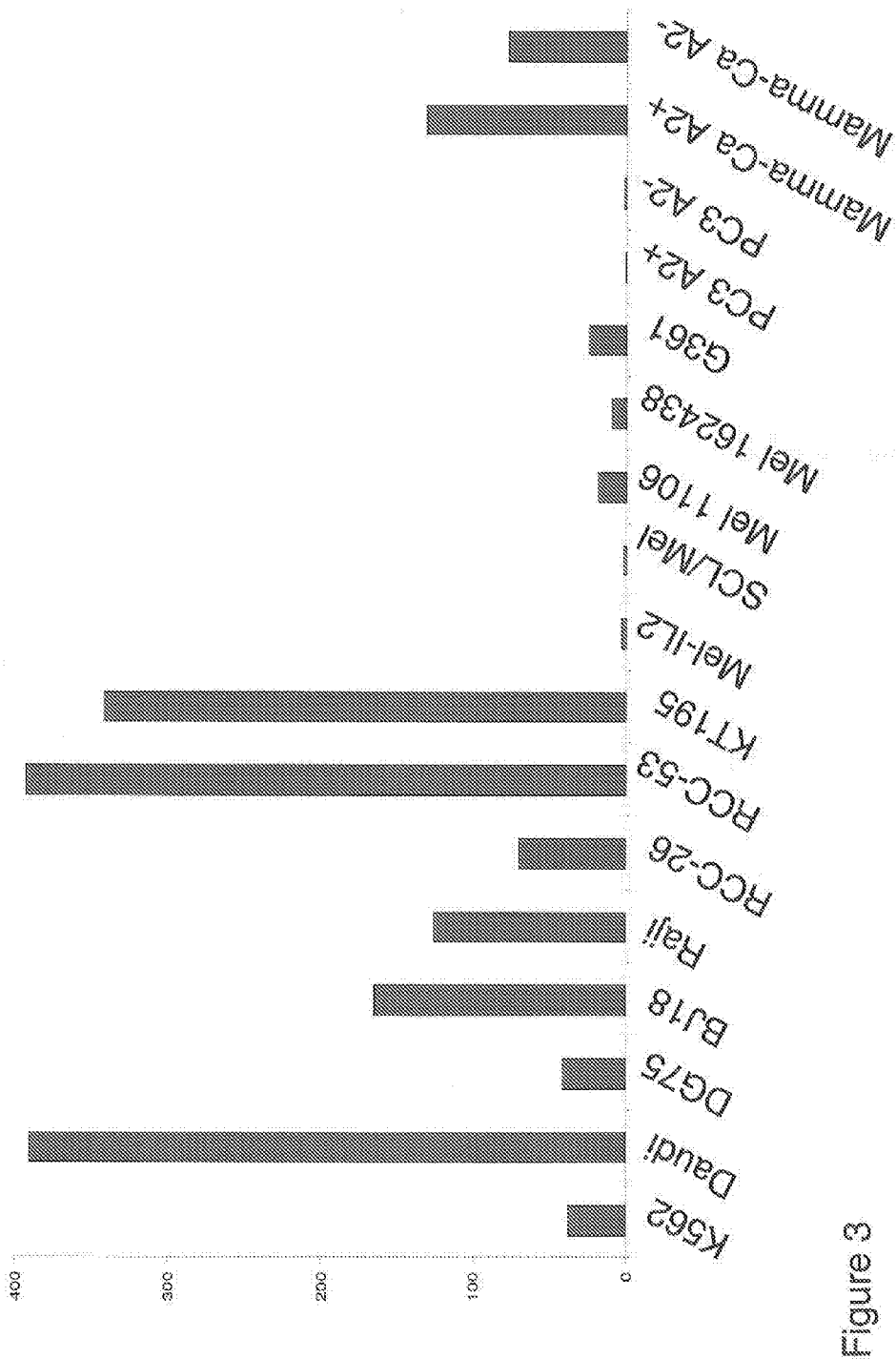
FIG. 3: Fold expression of FMNL1/KW13 mRNA in malignant cell lines compared to skeletal muscle investigated by quantitative RT-PCR.
Figure 4:
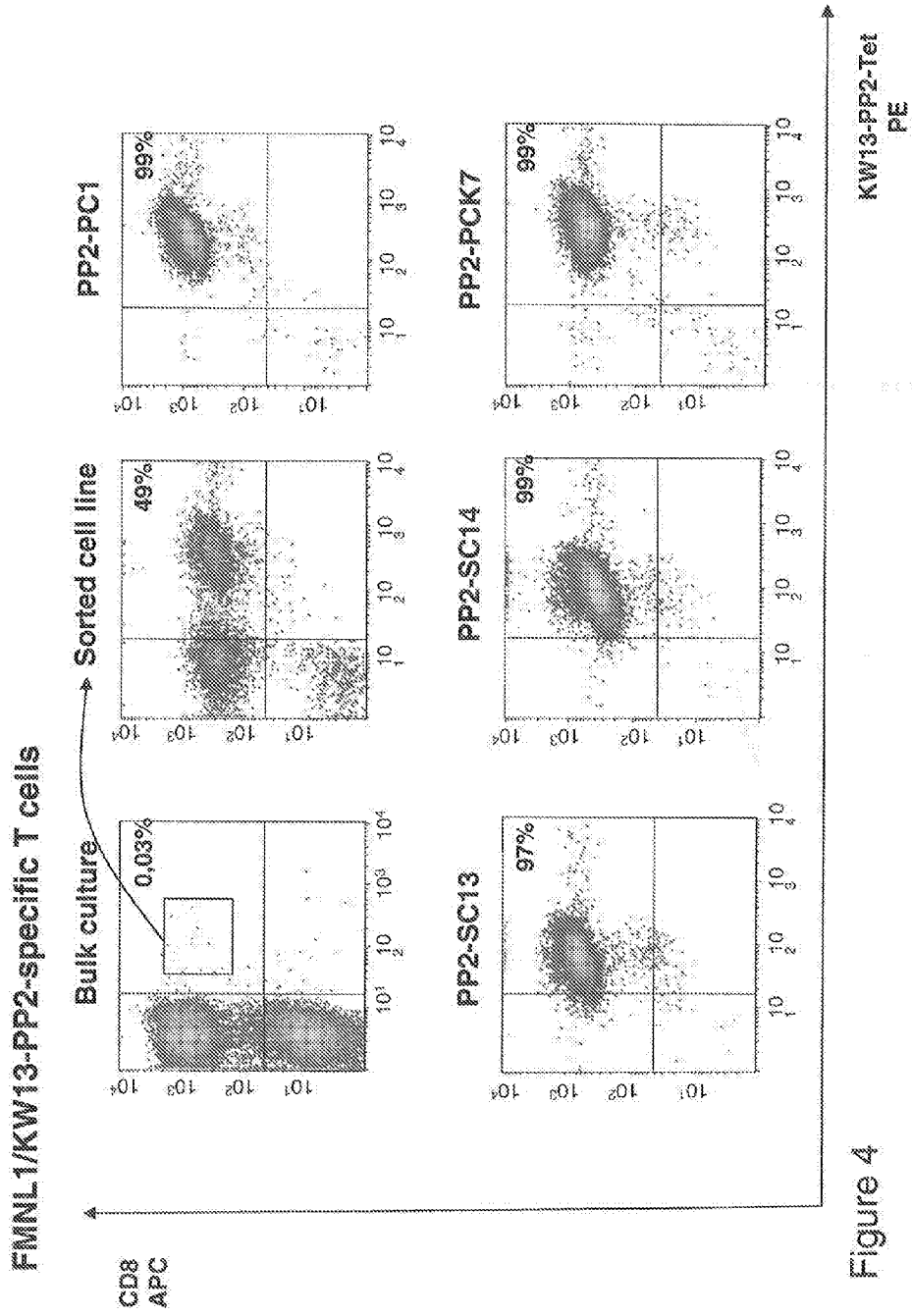
FIG. 4: Enrichment of allorestricted KW13-PP2-specific T cells by Tetramer sorting. Bulk cultures before sorting, enriched T cell lines and 4 cloned T cells are stained with anti-human CD8 APC and KW13-PP2-Tetramer-PE.
Figure 5:
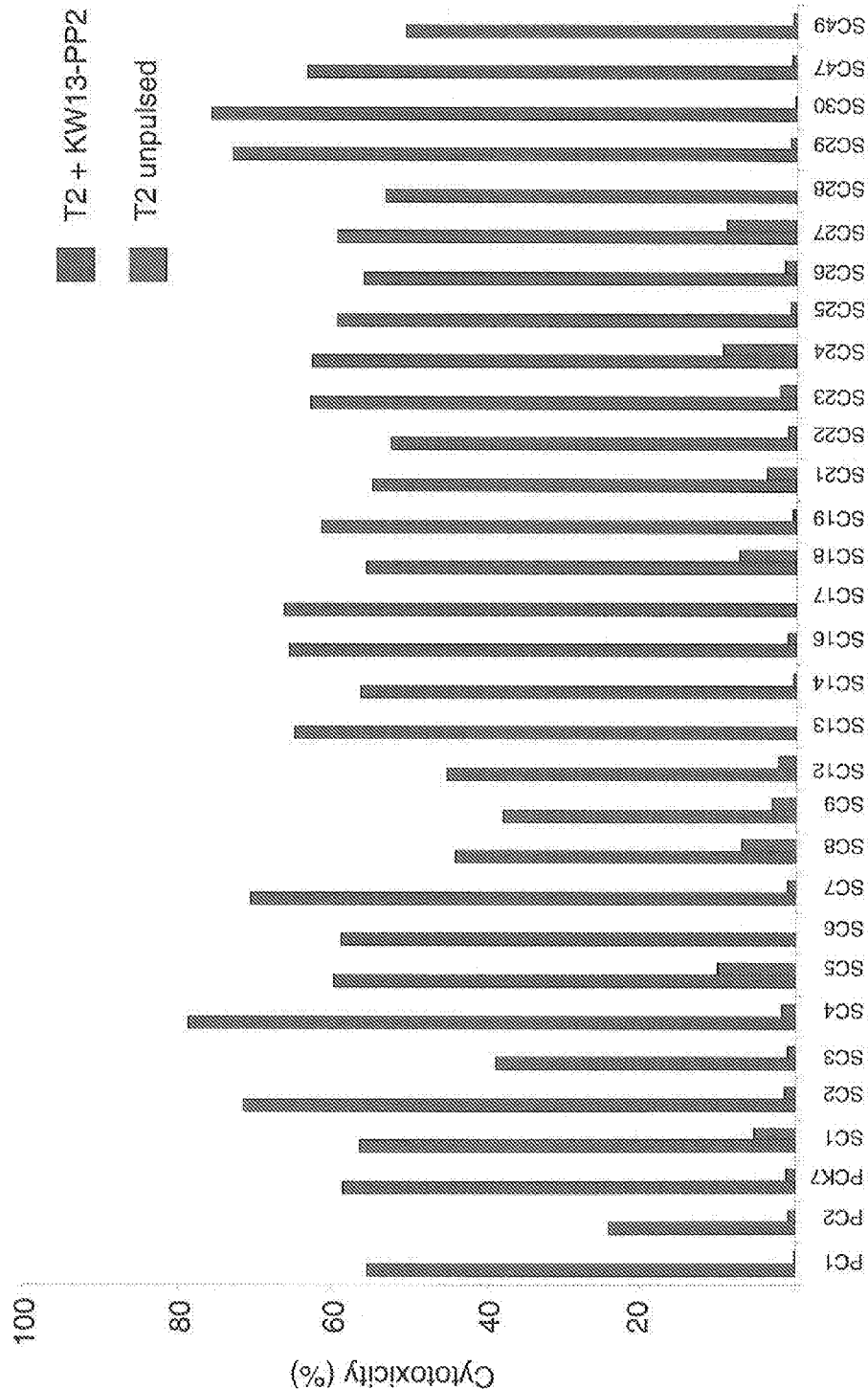
FIG. 5: Mini-Chromium-Assay to detect KW13-PP2-specific killing of cloned T cells. $^{51}$Cr-labeled targets are T2 cells pulsed with the specific peptide PP2 and unpulsed T2 cells as controls.
Figure 6:
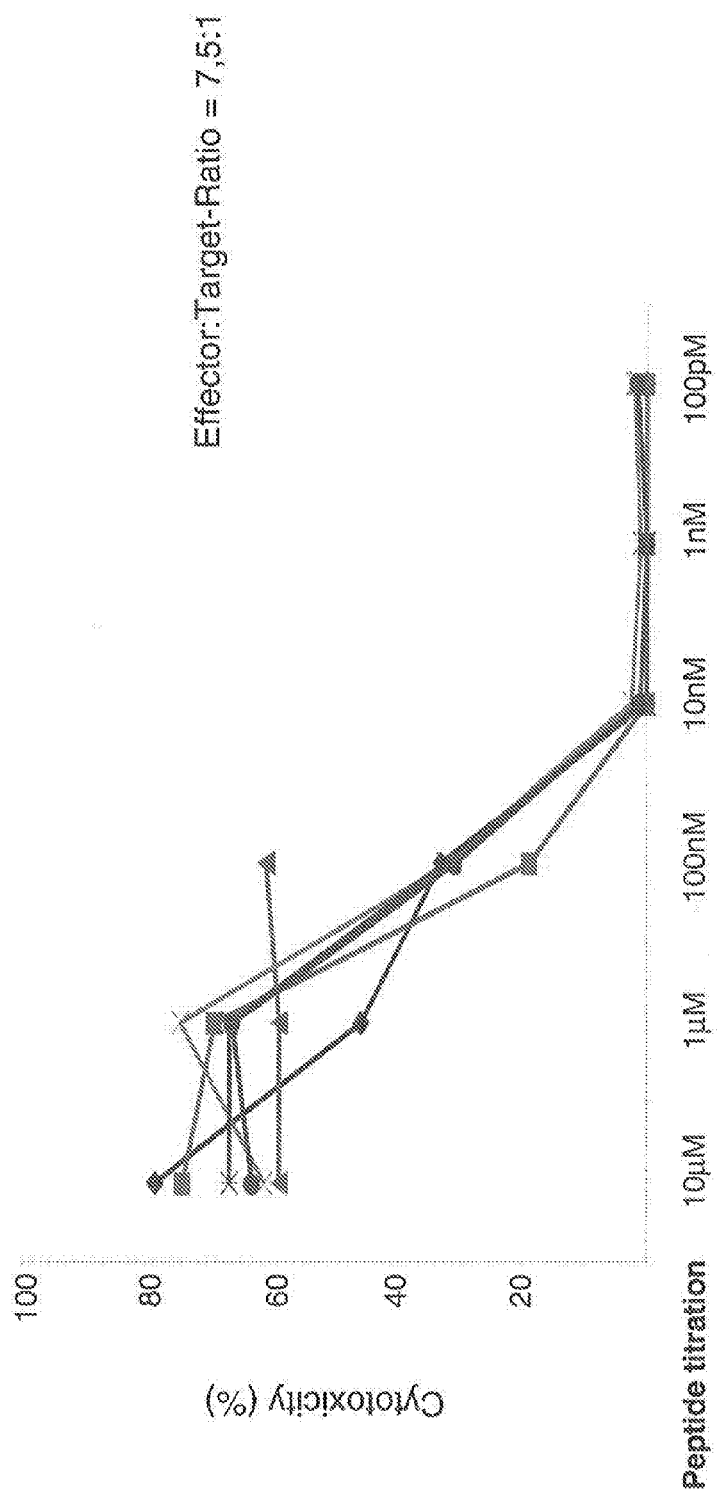
FIG. 6: Functional analysis of KW13-PP2 specific T cell lines and clones. Investigation of T cell affinity of 5 different T cell lines and clones in response to T2 cells pulsed with titrated concentrations of the specific peptide KW13-PP2.
Figure 7:
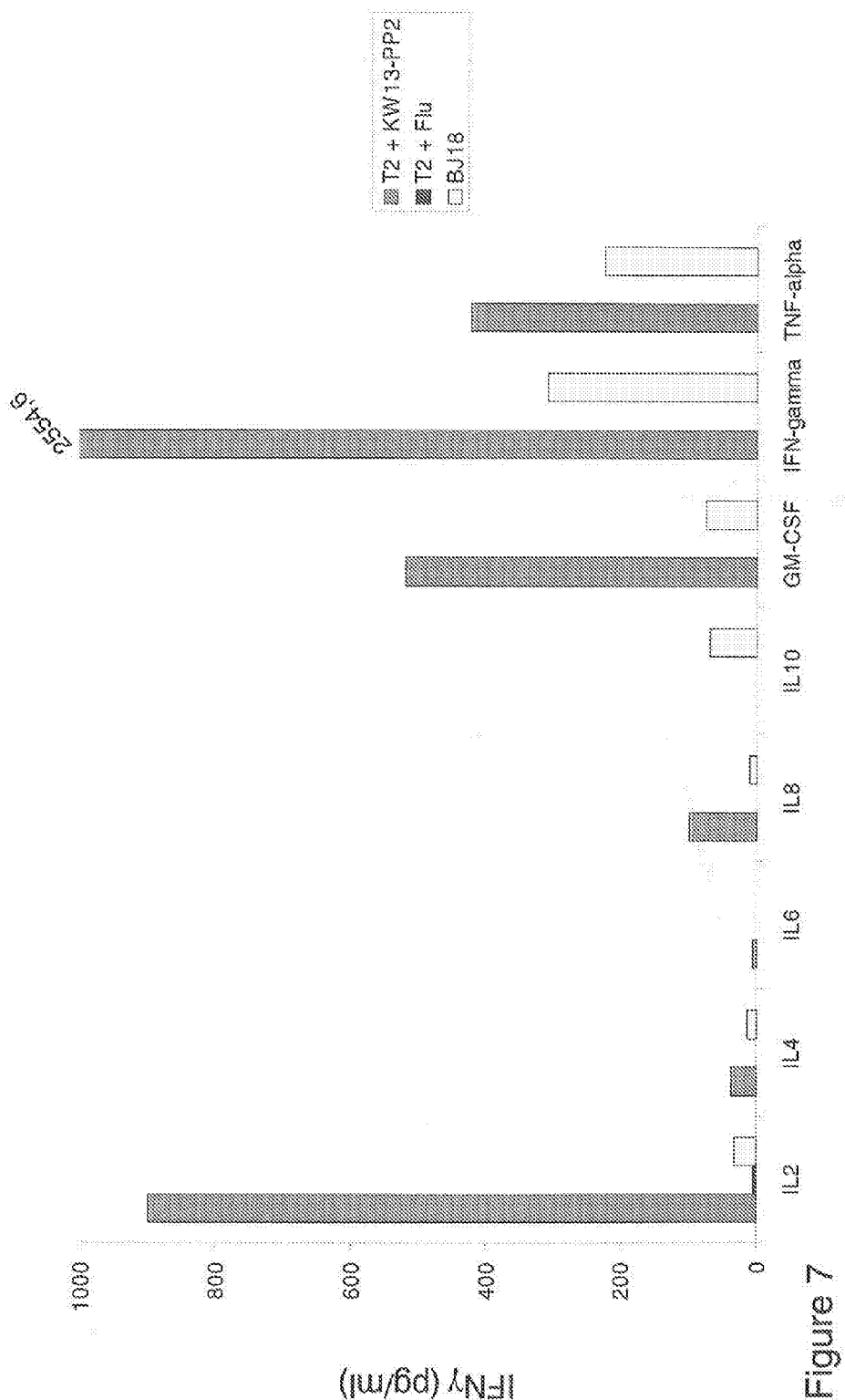
FIG. 7: Functional analysis of KW13-PP2 specific T cell lines and clones. Bioplex-Multianalysis ELISA of PP2-SC22 in response to T2 cells pulsed with the specific peptide KW13-PP2, T2 cells pulsed with the Flu-peptide (MP58) and BJ18 lymphoma cells.
Figure 8:
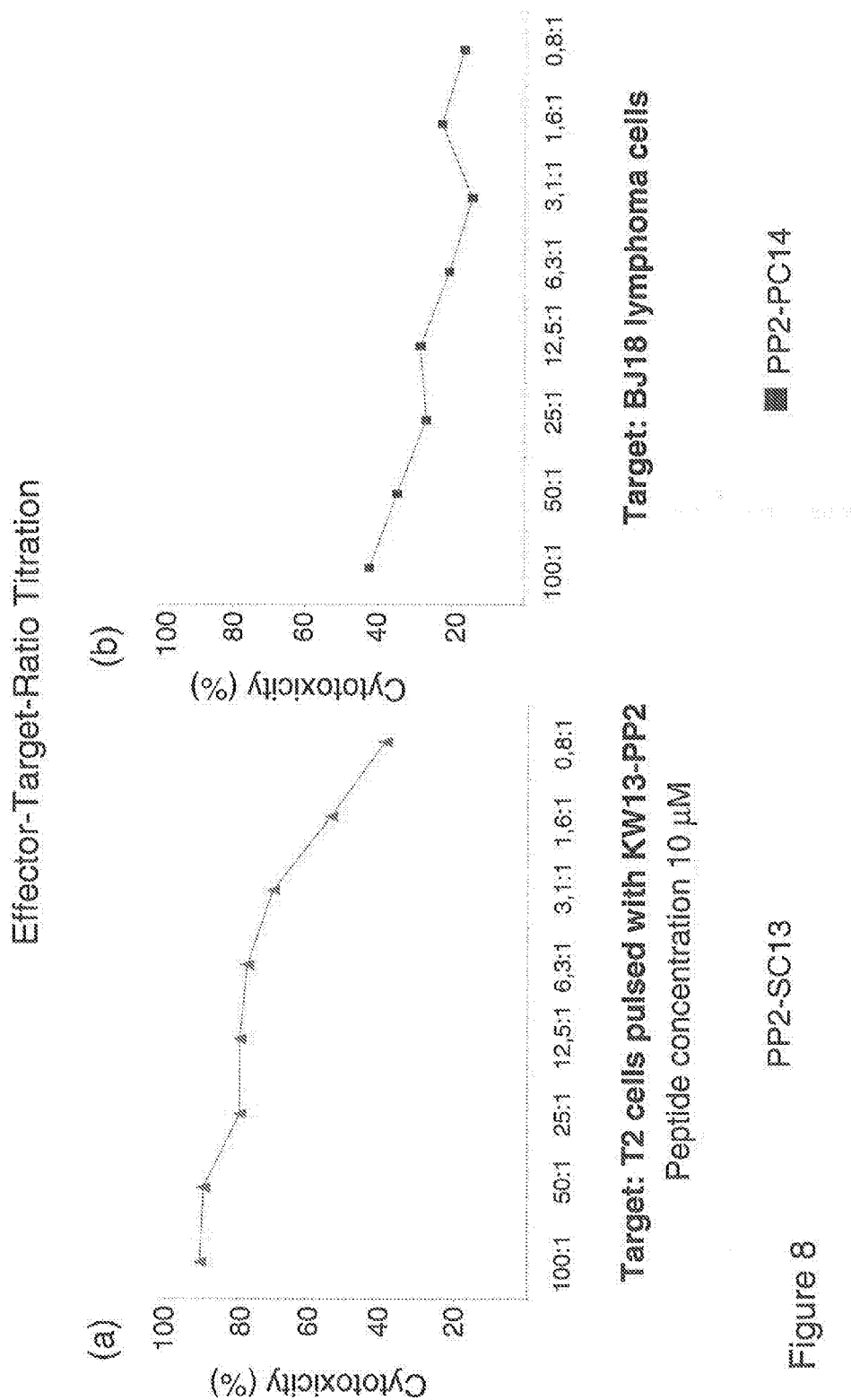
FIG. 8: Titration of the Effector:Target-Ratio with (a) PP2-SC13 as effector cells and KW13-PP2-pulsed T2 cells as targets and (b) PP2-SC14 as effector cells and BJ18 lymphoma cells as targets.
Figure 9:
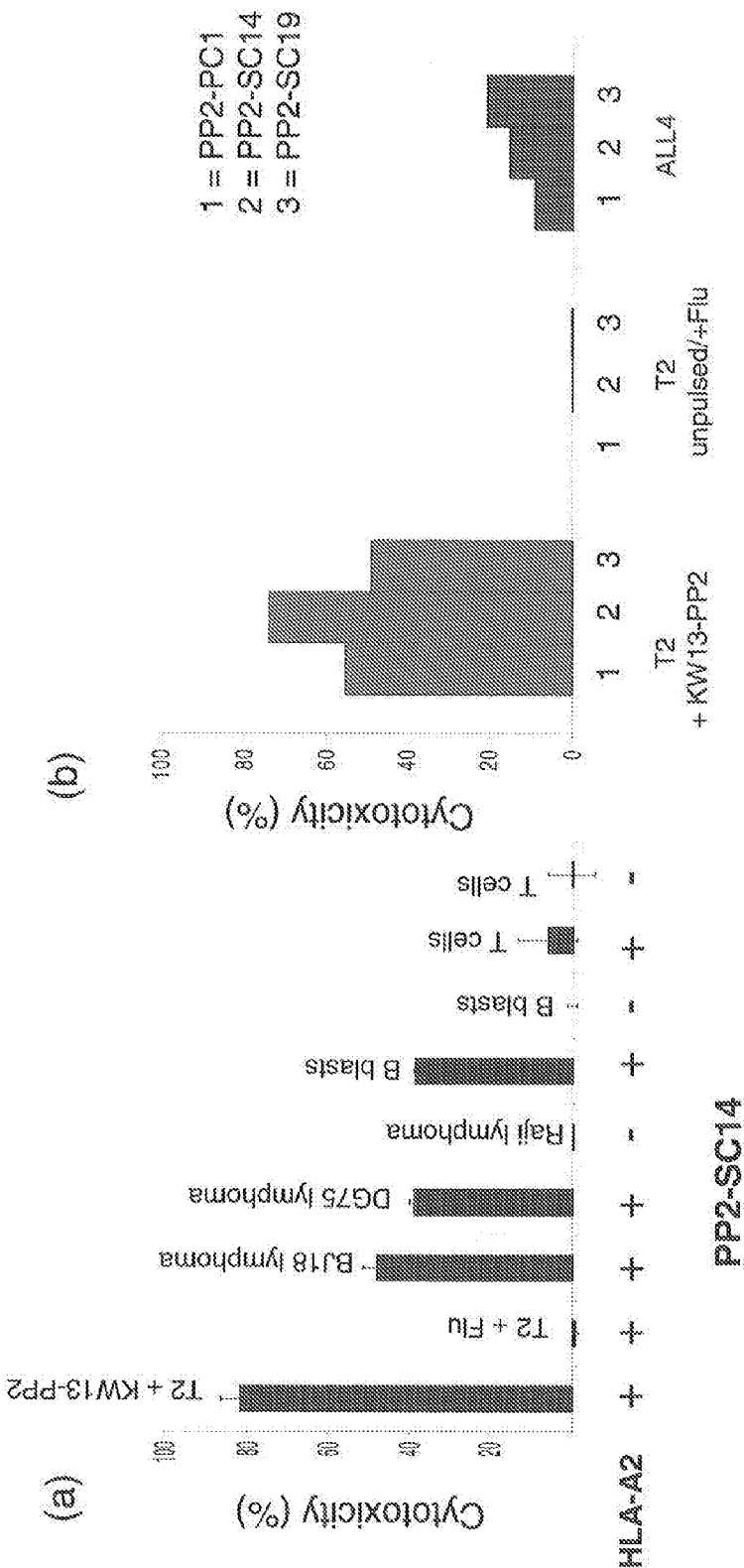
FIG. 9: Functional analysis of KW13-PP2 specific T cell lines and clones.
(a) Specific cytotoxicity of PP2-SC14 in response to pulsed T2 cells and different malignant cell lines and primary healthy cell material and (b) specific cytotoxicity of PP2-PC1, PP2-SC14 and PP2-SC19 against KW13-PP2-pulsed T2 cells, unpulsed T2 cells and acute lymphoblastic leukemia (ALL).
Figure 10:
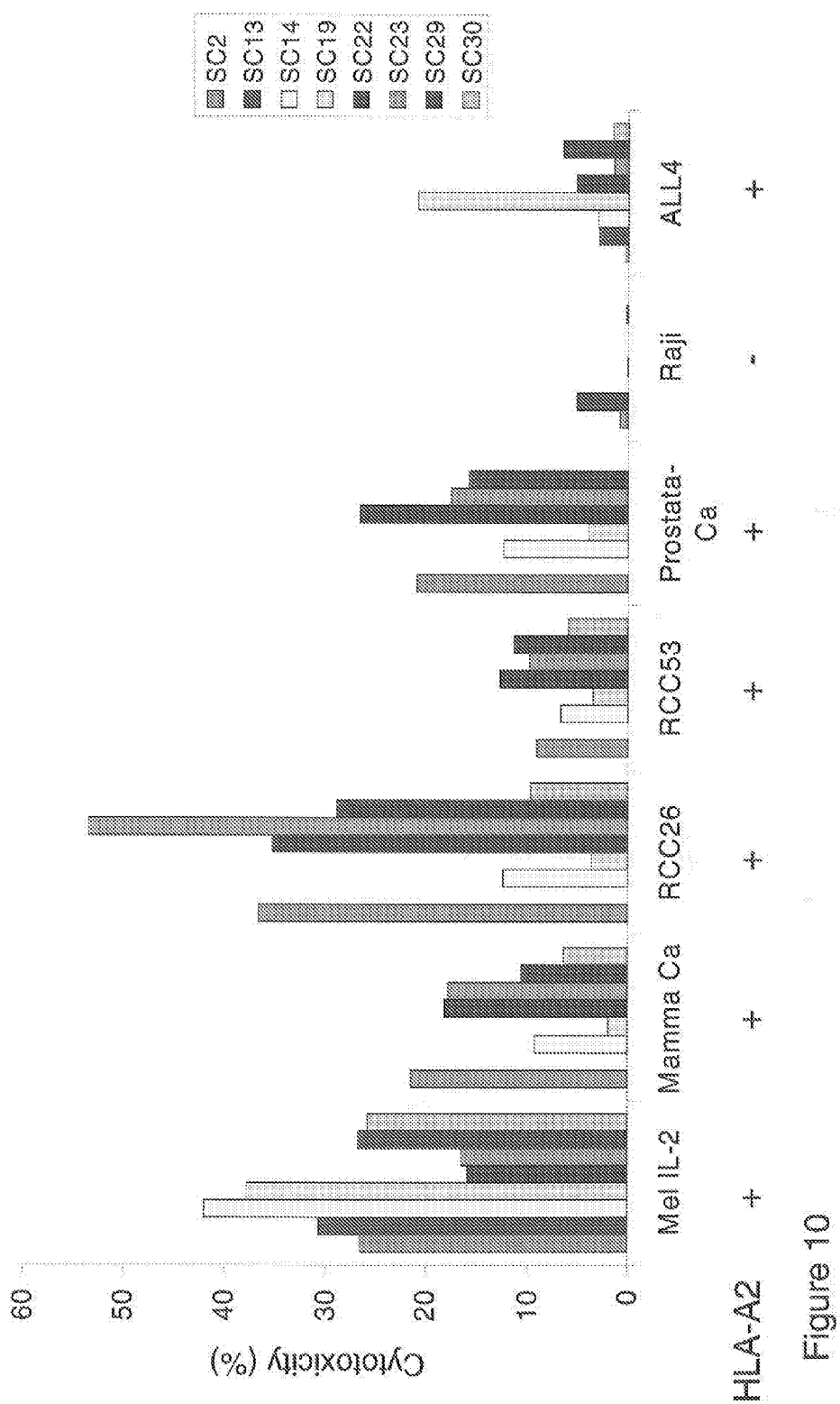
FIG. 10: Overview of specific cytotoxicity of cloned KW13-PP2-specific T cells against malignant cell lines and primary tumor material.
Figure 11:
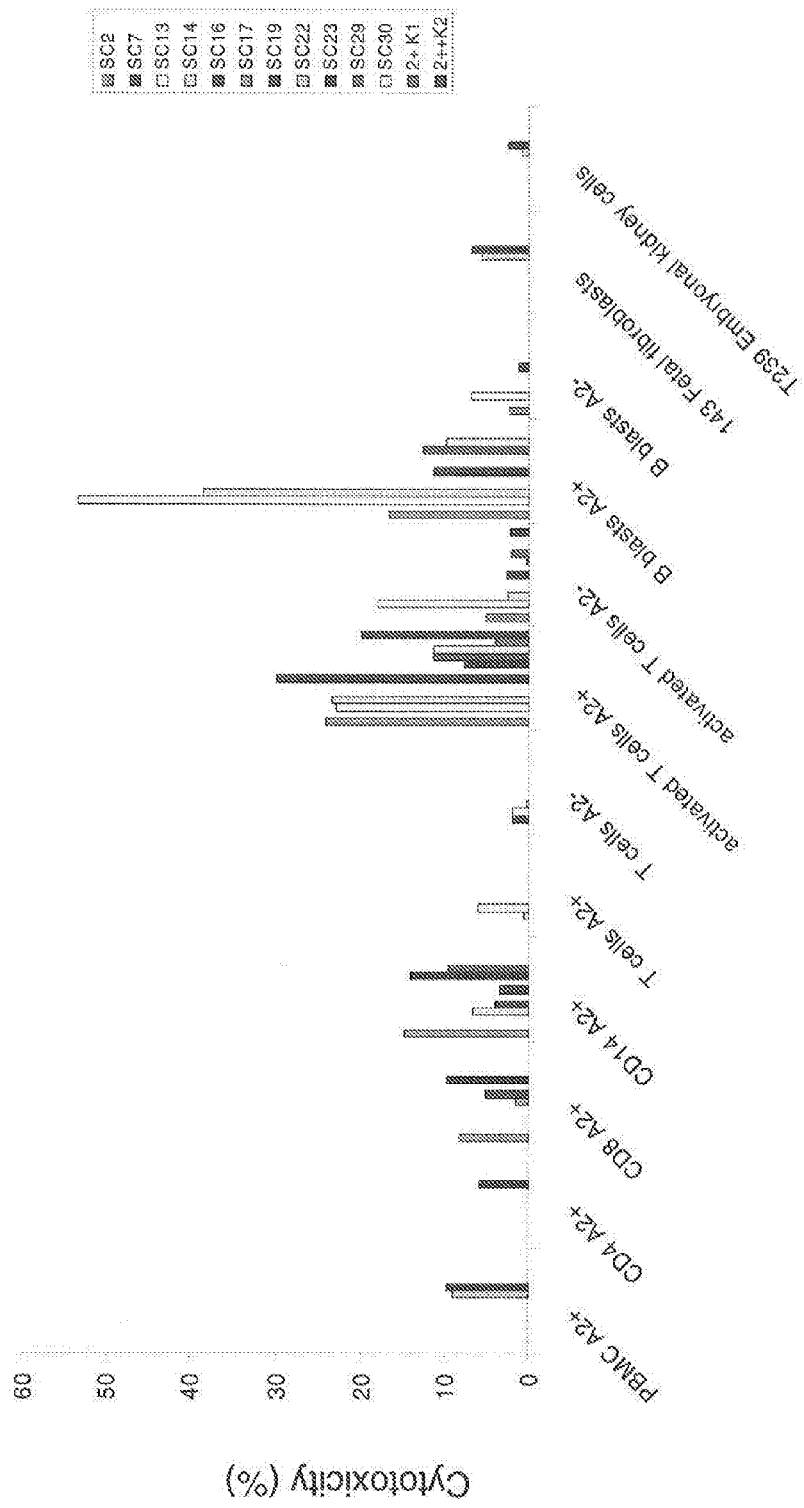
FIG. 11: Overview of specific cytotoxicity of cloned KW13-PP2-specific T cells against healthy PBMC subpopulations and cell line derived from healthy tissue.
Figure 12:
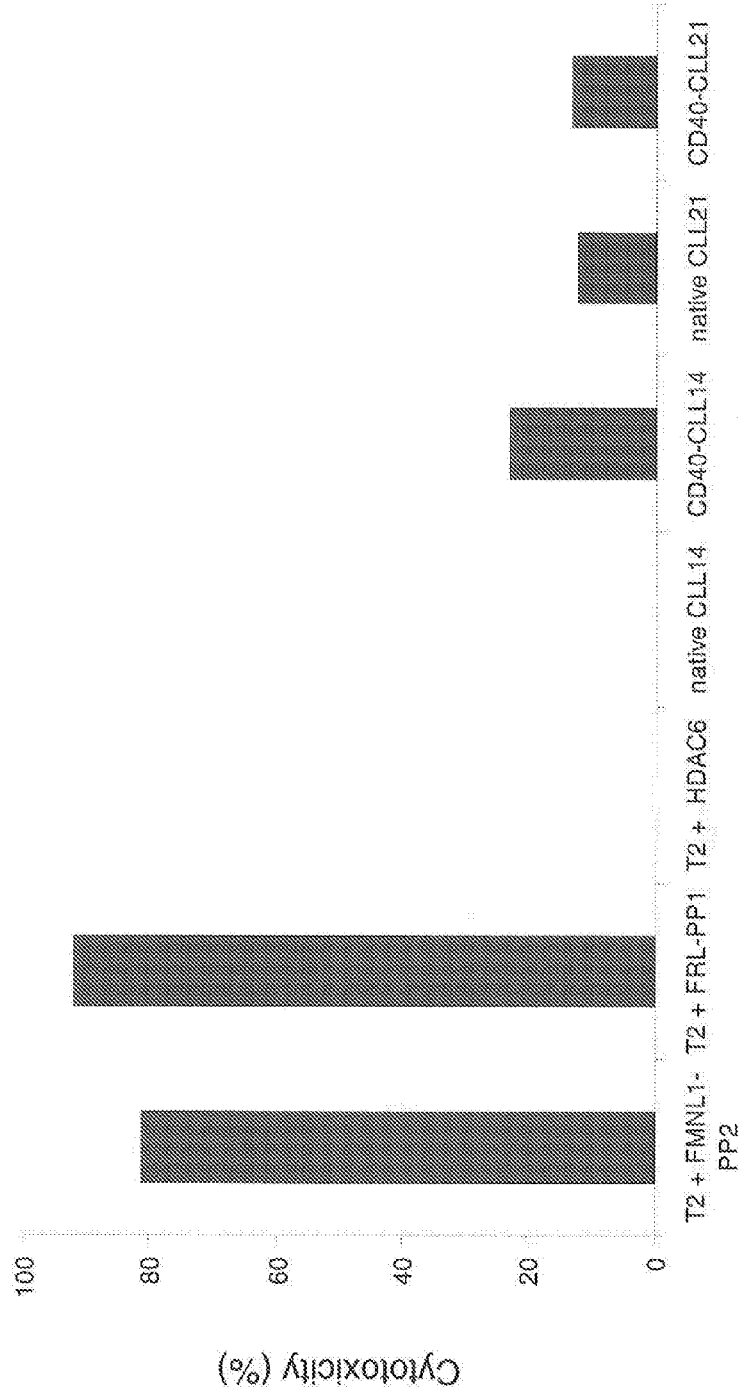
FIG. 12: Specific cytotoxicity of PP2-SC22 against T2 cells pulsed with the peptide FMNL1-PP2, the murine homologue FRL-PP1, a highly homologous peptide derived from HDAC6 as well as native and CD40-activated CLL cells.
Figure 14:
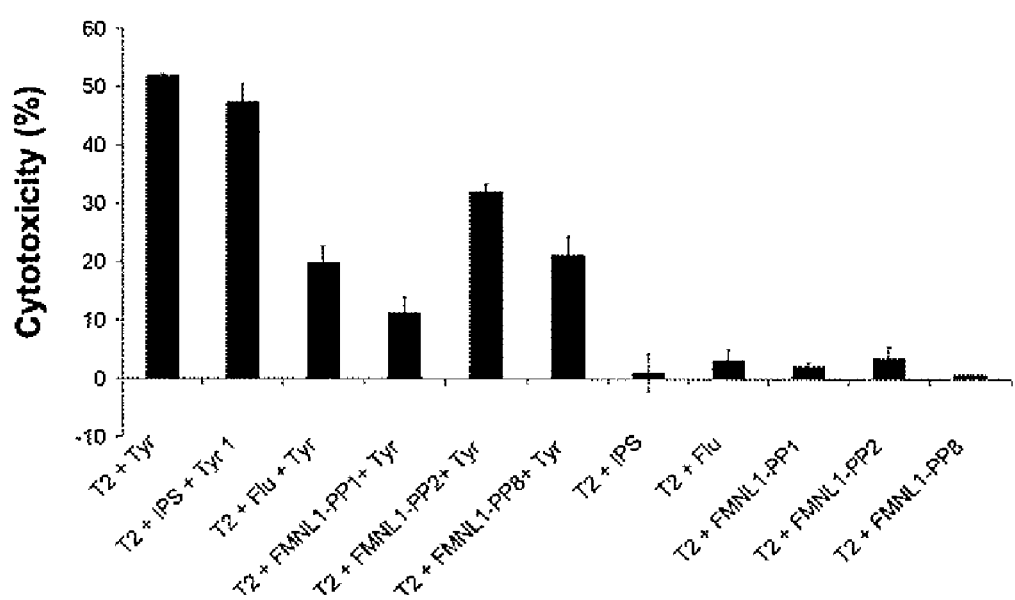
FIG. 14. Peptide competition assay. Peptide candidates derived from FMNL1 were investigated for their potential binding ability to HLA-A2. Therefore, different FMNL1- derived peptides were loaded on T2 cells and afterwards pulsed with the tyrosinase-derived peptide (Tyr). Flu was used as positive control. IPS as well as peptide pulsed T2 cells, which were afterwards not pulsed with tyrosinase, were used as negative controls. Tyrosinase-specific recognition was investigated by the tyrosinase-specific T-cell clone IVSB in a $^{51}$Cr-release assay at effector:target ratio of 2.5:1.

Allorestricted peptide-specific T cells should be directed against tumor associated antigens with specific characteristics. These antigens should have a most possibly restricted expression to the tumor cell to avoid side effects and should play an important role for vitality and growth of the tumor cell to reduce the risk of target down regulation. We previously identified 14 novel tumor associated antigens using the SEREX (serological identification by recombinant expression cloning) approach in CLL (8). These antigens have been extensively tested for their potential use as target antigens and we selected a few of them for our ongoing studies. FMNL1/KW13 (AF432213) is a formin related protein in leukocytes and has been first described using the SEREX approach in CLL (8). We investigated the mRNA expression of FMNL1/KW13 using quantitative RT-PCR. We observed expression of FMNL1 in healthy tissue mostly in PBMC and to a much lesser extent in bone marrow and thymus. However, we have not seen major expression in any healthy tissue (FIG. 1). In contrast, FMNL1/KW13 is highly overexpressed in 60% of CLL samples tested (FIG. 2a), some acute leukemia samples (FIG. 2b) and malignant cell lines (FIG. 3). Developing specific effectors against peptides derived from FMNL1/KW13 might be therefore highly useful for the development of immunotherapies against malignant lymphomas and also for the development of antirheumatic treatment tools based on the almost exceptional expression of FMNL1/KW13 in leukocytes.

Peptides derived from FMNL1 were selected using prediction algorithms for HLA-binding, proteasomal cleavage sites and TAP transportation (13-16). We are also investigating predicted peptide-antigen candidates of the B cell receptor α-chain (Table 1).

TABLE 1

Peptides derived from FMNL1/KW13 (or FRL) and B cell receptor α-chain selected for generation of allorestricted peptide-specific T cells

| Name | Sequence | |
|---|---|---|
| KW13-PP1 | VLLEYLAFA | (SEQ ID NO: 1) |
| KW13-PP2 | RLPERMTTL | (SEQ ID NO: 2) |
| KW13-PP6 | CVNEIALSL | (SEQ ID NO: 3) |
| KW13-PP7 | RLRLTESDKL | (SEQ ID NO: 4) |
| FRL | RLPERMNTL | (SEQ ID NO: 5) |
| BCR1 | GLQGTYQDV | (SEQ ID NO: 6) |
| BCR2 | YLGPGCQAL | (SEQ ID NO: 7) |
| BCR3 | GTYQDVGSL | (SEQ ID NO: 8) |

Generation of Allorestricted Peptide Specific T Cells

T2 cells which are defective in transporters associated with antigen-processing (TAP) can be efficiently loaded with exogenous HLA-A*0201 binding peptides and were pulsed with selected peptides at different concentrations. Mainly concentrations of 10 μM and 1 μM were used for pulsing. Peripheral blood mononuclear cells (PBMC) from HLA-A2-negative donors were isolated by Ficoll density gradient. T cells were negatively isolated using magnetic bead depletion (Dynal). T cells were then cultured with peptide-pulsed irradiated T2 cells at ratios of 1:10 to 1:100. Cytokines as IL-7 (5 ng/ml), IL-15 (5 ng/ml) and IL-2 (50 U/ml) were added. Restimulations were performed after 5-7 days using again peptide-pulsed T2 cells. Cultured T cells were stained with HLA-tetrameric complexes and anti-CD8 monoclonal antibodies and were sorted using a flow cytometry sorter. Sorted T cells were cloned by limiting dilution as well as cultured in oligoclonal T cell lines. These clones and unstimulated T cell lines were unspecifically restimulated with allogeneic feeder cells (PBMC pools) and OKT3. T cells were analyzed for their specificity using $^{51}$Cr release assays, ELISA and tetramer staining.

Using this approach we were able to generate allorestricted peptide-specific T cells with specificity against the selected peptide KW13-PP2. These T cells also show specific cytotoxicity against malignant cell lines, chronic lymphocytic leukaemia cells, acute lymphoblastic leukaemia cells and also activated lymphocytes (FIG. 4-12).

The inventors are currently investigating the T cell receptor (TCR) repertoire of the generated T cell lines and clones. One example is the oligoclonal T cell line PP2-PC1, presenting two α-chains and three β-chains which are involved in peptide-specific killing of allorestricted T cells (Table 2). Subcloning of this T cell line has been performed to identify the specific TCR chain responsible for peptide-specific killing. Clone SC22 shows a singular α-(Vα14J41) and β-chain (Vβ14J2.5) which is already represented in the T cell line PP2-PC1, demonstrating the fundamental functional role of these two CDR3-regions in allorestricted FMNL1-PP2-specificity (Table 3).

TABLE 2

T cell receptor analysis of PP2-PC1 demonstrating
the pattern of an oligoclonal T cell line

| Nomenclature | Alignment for V-gene | Alignment for J-gene | CDR3 region cDNA sequence | CDR3 region Amino acid sequence |
|---|---|---|---|---|
| TCR-α-chains: | | | | |
| 1. IMGT | TRAV38-2/DV8*01 | TRAJ41*01 | GCT TAT GAA AAT TCC GGG TAT GCA CTC AAC TTG (SEQ ID No: 15) | A Y E N S G Y A L N F (SEQ ID No: 9) |
| Arden et al. | Vα14 | J41 | GCT TAT GAA AAT TCC GGG TAT GCA CTC AAC TTC (SEQ ID No: 15) | A Y E N S G Y A L N F (SEQ ID No: 9) |
| 2. IMGT | TRAV21*02 | TRAJ21*01 | GCT GTG AGG CTA AGT ::C TTC AAC AAA TTT TAG TTT SEQ ID No: 16 | A V R L S # F N K F Y F SEQ ID NO: 10 |
| Arden et al. | Vα23 | J21 | GCT GTG AGG CTA AGT ::C TTC AAC AAA TTT TAC TTT SEQ ID No: 16 | A V R L S # F N K F Y F SEQ ID NO: 10 |
| TCR-β-chains: | | | | |
| 3. IMGT | TRBV7-4*01 | TRBJ2-3*01 | CAG CAG CTT ATT GCG GGA GGG CCT ACA GAT ACG CAG TAT TTT SEQ ID No: 17 | Q Q L I A G G P T D T Q Y P SEQ ID NO: 11 |
| Arden et al. | Vβ6.1 | Jβ2.3 | CAG CAG GTT ATT GCG GGA GGG CCT ACA GAT ACG CAG TAT TTT SEQ ID No: 17 | Q Q L I A G G P T D T Q Y F SEQ ID NO: 11 |
| 4. IMGT | TRBV7-4*01 | TRBJ2-3*01 | GCC AGC AGC TTA TTG CGG GAG GGC CT: ACA GAT ACG CAG TAT TTT SEQ ID No: 18 | A S S L L R E G # T D T Q Y F SEQ ID NO: 12 |
| Arden et al. | 4β6.1 | Jβ2.3 | GCC AGC AGC TTA TTG GCG GAG GGC CT: ACA GAT ACG CAG TAT TTT SEQ ID No: 18 | A S S L L T E G # T D T Q Y F SEQ ID NO: 12 |
| 5. IMGT | TRBV27*01 | TRBJ2-5*01 | GCC AGC AGT TTT CTG GGG GAG ACC CAG TAG TTC SEQ ID No: 19 | A S S F L G E T Q Y F SEQ ID NO: 13 |
| Arden et al. | vβ14 | Jβ2.5 | GCC AGC AGT TTT CTG GGG GAG ACC CAG TAC TTC SEQ ID No: 19 | A S S F L G E T Q Y F SEQ ID NO: 13 |
| 6. IMGT | TCRBV11-2*01 | TRBJ2-7*01 | GCC AGC AGC TTA GCT TTC GGA CAG GGG GGC TCC | A S S L A F G Q G R S Y E Q Y F |

TABLE 2-continued

T cell receptor analysis of PP2-PC1 demonstrating
the pattern of an oligoclonal T cell line

| Nomenclature | Alignment for V-gene | Alignment for J-gene | CDR3 region cDNA sequence | CDR3 region Amino acid sequence |
|---|---|---|---|---|
| | | | TAC GAG CAG TAC TTG SEQ ID No: 20 | SEQ ID NO: 14 |
| Arden et al. Vβ21 | | Jβ2.7 | GCC AGC AGC TTA GCT TTC GGA CAG GGG GGC TCC TAC GAG CAG TAC TTC SEQ ID No: 20 | A S S L A F G Q G R S Y E Q Y F SEQ ID NO: 14 |

TABLE 3

T cell clone SC22 shows the following
pattern for α- and β-chain (Vα14J41; Vβ14J2.5):

| Variable chain | CDR3 region cDNA sequence | CDR3 region Amino acid sequence |
|---|---|---|
| vα14J41 (Arden et al.) | GCT TAT GAA AAT TCC GGG TAT GCA CTC AAC TTC (SEQ ID No: 15) | A Y E N S G Y A L N F (SEQ ID No: 9) |
| Vβ14J2.5 (Arden et al.) | GCC AGC AGT TTT CTG GGG GAG ACC GAG TAC TTC (SEQ ID NO: 19) | A S S F L G E T Q Y F SEQ ID NO: 13 |

TABLE 4

Prediction scores of selected peptides derived from FMNL1

| Peptide | HLA-A2 binding | | TAP-transportation* | | Proteasomal cleavage sites† |
|---|---|---|---|---|---|
| | SYFPEITHY[28] | BIMAS[29] | TAP[30] | TAP[31] | PAProC II[32] |
| FMNL1-PP1 VLLEYLAFA SEQ ID NO: 1 | 26 | 1620 | 1/0 | 0/1 | +++(3) |
| FMNL1-PP2 RLPERMTTL SEQ ID NO: 2 | 24 | 201 | 4/0 | 2/1 | ++(2) |
| FMNL1-PP3 ELQEQVALL SEQ ID NO: 22 | 25 | 15 | 2/2 | 1/2 | +++(2) |
| FMNL1-PP4 FINIVVHSV SEQ ID NO: 23 | 27 | 101 | 2/2 | 2/1 | +++(2) |
| FMNL1-PP5 QSLDALLEM SEQ ID NO: 24 | 14 | 1, 1 | 1/1 | 0/0 | −(1) |
| FMNL1-PP6 CVNEIALSL SEQ ID NO: 3 | 20 | 7, 7 | 2/1 | 1/0 | ++(1) |

TABLE 4-continued

Prediction scores of selected peptides derived from FMNL1

| Peptide | HLA-A2 binding | | TAP-transportation* | | Proteasomal cleavage sites† |
|---|---|---|---|---|---|
| | SYFPEITHY[28] | BIMAS[29] | TAP[30] | TAP[31] | PAProC II[32] |
| FMNL1-PP7 RLRLTESDKL SEQ ID NO: 4 | 22 | 20, 4 | 2/1 | 2/1 | ++(2) |
| PMNL1-PP8 TLLHYLVKV SEQ ID NO: 21 | 31 | 592 | 2/0 | 1/1 | ++(4) |

*Number of favorable versus (/) unfavorable amino acids
†Probability of cleavage at the C-terminus: +++ very strong. ++ strong, + weak, − improbable, (number of predicted cute within the peptide)

LITERATURE (1) Maloney D. G., A. J. Grillo-Lopez, et al. (1997). IDEC-C2B8 (Rituximab) anti-CD20 monoclonal antibody therapy in patients with relapsed low-grade non-Hodgkin's lymphoma. Blood 90 (6): 2188-2195.

(2) Rai K. R., C. E. Freter, et al. (2002). Alemtuzumab in previously treated chronic lymphocytic leukemia patients who also had received fludarabine. J Clin Oncol 20 (18): 3891-3897.

(3) Marks D. I., R. Lush, et al. (2002). The toxicity and efficacy of donor lymphocyte infusions given after reduced-intensity conditioning allogeneic stem cell transplantation. Blood 100 (9):3108-14.

(4) Khouri I. F., M. S. Lee, et al. (2003). Nonablative allogeneic stem-cell transplantation for advanced/recurrent mantle-cell lymphoma. J Clin Oncol. 21 (23):4407-12.

(5) Schetelig J., C. Thiede, et al. (2003). Evidence of a graft-versus-leukemia effect in chronic lymphocytic leukemia after reduced-intensity conditioning and allogeneic stem cell transplantation: the Cooperative German Transplant Study Group. J Clin Oncol 21 (14): 2747-2753.

(6) Heath W. R., M. E. Hurd, et al. (1989). Peptide-dependent recognition of H-2 Kb by alloreactive cytotoxic T lymphocytes. Nature 341 (6244): 749-752.

(7) Sadovnikova E., H. J. Stauss (1996). Peptide-specific cytotoxic T lymphocytes restricted by nonself major histocompatibility complex class I molecules: reagents for tumor immunotherapy. PNAS 93 (23): 13114-13118.

(8) Krackhardt A. M.*, M. Witzens*, et al. (2002a). Identification of tumor associated antigens in chronic lymphocytic leukemia by SEREX. Blood 100 (6): 2123-2131. [*first coauthorship]

(9) Engels B., E. Noessner, et al. (2005). Redirecting human T lymphocytes toward renal cell carcinoma specificity by retroviral transfer of T cell receptor genes. Hum Gene Ther 16 (7): 799-810.

(10) Schendel D. J., R. Oberneder, et al. (1997). Cellular and molecular analyses of major histocompatibility complex (MHC) restricted and non-MHC-restricted effector cells recognizing renal cell carcinomas: problems and perspectives for immunotherapy. J Mol Med 75 (6): 400-413.

(11) Yee C., P. A. Savage, et al. (1999). Isolation of high avidity melanoma-reactive CTL from heterogenous populations using peptide-MHC tetramers. J Immunol 162 (4): 2227-2234.

(12) Becker C., H. Pohla, et al. (2001). Adoptive tumor therapy with T lymphocytes enriched through an IFN-gamma capture assay. Nat Med 7 (10): 1159-1162.

(13) Parker K. C., M. A. Bednarek, et al. (1994). Scheme for ranking potential HLA-A*0201 binding peptides based on independent binding of individual peptide side chains. J Immunol 152 (1): 163-175.

(14) Raammensee H., J. Bachmann, et al. (1999). SYFPEITHI: database for MHC ligands and peptide motifs; Immunogenetics 50 (3-4): 213-219.

(15) Kuttler C., A. K. Nussbaum, et al. (2000). An algorithm for the prediction of proteasomal cleavages. J Mol Biol 298 (3): 417-429.

(16) Larsen M. V., C. Lundegaard, et al. (2005). An integrative approach to CTL epitope prediction: A combined algorithm integrating MHC class I binding, TAP transport efficiency, and proteasomal cleavage predictions. Eur J Immunol 35 (8): 2295-2303.

(17) Arden B., S. Clark, et al. (1995). Human T-cell receptor variable gene segment families. Immunogenetics 42: 455-500.

The invention claimed is:

1. An isolated T cell receptor (TCR) that specifically recognizes an antigenic peptide bound to human leukocyte antigen A2 (HLA-A2), wherein the antigenic peptide has the amino acid sequence of SEQ ID NO: 2.

* * * * *

SEQUENCE LISTING

<160> NUMBER OF SEQ ID NOS: 25

<210> SEQ ID NO 1
<211> LENGTH: 9
<212> TYPE: PRT
<213> ORGANISM: Artificial Sequence
<220> FEATURE:
<223> OTHER INFORMATION: Artificially synthesized antigenic peptide derived from FMNL1/KW13

<400> SEQUENCE: 1

Val Leu Leu Glu Tyr Leu Ala Phe Ala
1               5

<210> SEQ ID NO 2
<211> LENGTH: 9
<212> TYPE: PRT
<213> ORGANISM: Artificial Sequence
<220> FEATURE:
<223> OTHER INFORMATION: Artificially synthesized antigenic peptide
      derived from FMNL1/KW13

<400> SEQUENCE: 2

Arg Leu Pro Glu Arg Met Thr Thr Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Artificially synthesized antigenic peptide
      derived from FMNL1/KW13

<400> SEQUENCE: 3

Cys Val Asn Glu Ile Ala Leu Ser Leu
1               5

<210> SEQ ID NO 4
<211> LENGTH: 10
<212> TYPE: PRT
<213> ORGANISM: Artificial Sequence
<220> FEATURE:
<223> OTHER INFORMATION: Artificially synthesized antigenic peptide
      derived from FMNL1/KW13

<400> SEQUENCE: 4

Arg Leu Arg Leu Thr Glu Ser Asp Lys Leu
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Artificially synthesized antigenic peptide
      derived from FMNL1/KW13

<400> SEQUENCE: 5

Arg Leu Pro Glu Arg Met Asn Thr Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Artificially synthesized antigenic peptide
      derived from B cell receptor alpha chain

<400> SEQUENCE: 6

Gly Leu Gln Gly Thr Tyr Gln Asp Val
1               5

<210> SEQ ID NO 7
<211> LENGTH: 9
<212> TYPE: PRT

```
<213> ORGANISM: Artificial Sequence
<220> FEATURE:
<223> OTHER INFORMATION: Artificially synthesized antigenic peptide
      derived from B cell receptor alpha chain

<400> SEQUENCE: 7

Tyr Leu Gly Pro Gly Cys Gln Ala Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Artificially synthesized antigenic peptide
      derived from B cell receptor alpha chain

<400> SEQUENCE: 8

Gly Thr Tyr Gln Asp Val Gly Ser Leu
1               5

<210> SEQ ID NO 9
<211> LENGTH: 11
<212> TYPE: PRT
<213> ORGANISM: Artificial Sequence
<220> FEATURE:
<223> OTHER INFORMATION: Artificially synthesized CDR3 region of TCR

<400> SEQUENCE: 9

Ala Tyr Glu Asn Ser Gly Tyr Ala Leu Asn Phe
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Artificially synthesized CDR3 region of TCR
<220> FEATURE:
<221> NAME/KEY: misc_feature
<222> LOCATION: (6)..(6)
<223> OTHER INFORMATION: Xaa can be any naturally occurring amino acid

<400> SEQUENCE: 10

Ala Val Arg Leu Ser Xaa Phe Asn Lys Phe Tyr Phe
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Artificially synthesized CDR3 region of TCR

<400> SEQUENCE: 11

Gln Gln Leu Ile Ala Gly Gly Pro Thr Asp Thr Gln Tyr Phe
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Artificially synthesized CDR3 region of TCR
<220> FEATURE:
<221> NAME/KEY: misc_feature
<222> LOCATION: (9)..(9)
<223> OTHER INFORMATION: Xaa can be any naturally occurring amino acid

<400> SEQUENCE: 12
```

-continued

Ala Ser Ser Leu Leu Arg Glu Gly Xaa Thr Asp Thr Gln Tyr Phe
1               5                   10                  15

<210> SEQ ID NO 13
<211> LENGTH: 11
<212> TYPE: PRT
<213> ORGANISM: Artificial Sequence
<220> FEATURE:
<223> OTHER INFORMATION: Artificially synthesized CDR3 region of TCR

<400> SEQUENCE: 13

Ala Ser Ser Phe Leu Gly Glu Thr Gln Tyr Phe
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Artificially synthesized CDR3 region of TCR

<400> SEQUENCE: 14

Ala Ser Ser Leu Ala Phe Gly Gln Gly Arg Ser Tyr Glu Gln Tyr Phe
1               5                   10                  15

<210> SEQ ID NO 15
<211> LENGTH: 33
<212> TYPE: DNA
<213> ORGANISM: Artificial Sequence
<220> FEATURE:
<223> OTHER INFORMATION: Artificially synthesized CDR3 region of TCR

<400> SEQUENCE: 15
gcttatgaaa attccgggta tgcactcaac ttc                                   33

<210> SEQ ID NO 16
<211> LENGTH: 36
<212> TYPE: DNA
<213> ORGANISM: Artificial Sequence
<220> FEATURE:
<223> OTHER INFORMATION: Artificially synthesized CDR3 region of TCR
<220> FEATURE:
<221> NAME/KEY: misc_feature
<222> LOCATION: (16)..(17)
<223> OTHER INFORMATION: n is a, c, g, or t

<400> SEQUENCE: 16
gctgtgaggc taagtnnctt caacaaattt tacttt                                36

<210> SEQ ID NO 17
<211> LENGTH: 42
<212> TYPE: DNA
<213> ORGANISM: Artificial Sequence
<220> FEATURE:
<223> OTHER INFORMATION: Artificially synthesized CDR3 region of TCR

<400> SEQUENCE: 17
cagcagctta ttgcgggagg gcctacagat acgcagtatt tt                         42

<210> SEQ ID NO 18
<211> LENGTH: 45
<212> TYPE: DNA
<213> ORGANISM: Artificial Sequence
<220> FEATURE:
<223> OTHER INFORMATION: Artificially synthesized CDR3 region of TCR
<220> FEATURE:
<221> NAME/KEY: misc_feature
<222> LOCATION: (27)..(27)

-continued

<223> OTHER INFORMATION: n is a, c, g, or t

<400> SEQUENCE: 18
gccagcagct tattgcggga gggcctnaca gatacgcagt atttt         45

<210> SEQ ID NO 19
<211> LENGTH: 33
<212> TYPE: DNA
<213> ORGANISM: Artificial Sequence
<220> FEATURE:
<223> OTHER INFORMATION: Artificially synthesized CDR3 region of TCR

<400> SEQUENCE: 19
gccagcagtt ttctggggga gacccagtac ttc         33

<210> SEQ ID NO 20
<211> LENGTH: 48
<212> TYPE: DNA
<213> ORGANISM: Artificial Sequence
<220> FEATURE:
<223> OTHER INFORMATION: Artificially synthesized CDR3 region of TCR

<400> SEQUENCE: 20
gccagcagct tagctttcgg acagggcgc tcctacgagc agtacttc         48

<210> SEQ ID NO 21
<211> LENGTH: 9
<212> TYPE: PRT
<213> ORGANISM: Artificial Sequence
<220> FEATURE:
<223> OTHER INFORMATION: Artificially synthesized antigenic peptide
      derived from FMNL1/KW13

<400> SEQUENCE: 21

Thr Leu Leu His Tyr Leu Val Lys Val
1               5

<210> SEQ ID NO 22
<211> LENGTH: 9
<212> TYPE: PRT
<213> ORGANISM: Artificial Sequence
<220> FEATURE:
<223> OTHER INFORMATION: Artificially synthesized antigenic peptide
      derived from FMNL1/KW13

<400> SEQUENCE: 22

Glu Leu Gln Glu Gln Val Ala Leu Leu
1               5

<210> SEQ ID NO 23
<211> LENGTH: 9
<212> TYPE: PRT
<213> ORGANISM: Artificial Sequence
<220> FEATURE:
<223> OTHER INFORMATION: Artificially synthesized antigenic peptide
      derived from FMNL1/KW13

<400> SEQUENCE: 23

Phe Ile Asn Ile Val Val His Ser Val
1               5

<210> SEQ ID NO 24
<211> LENGTH: 9
<212> TYPE: PRT
<213> ORGANISM: Artificial Sequence
<220> FEATURE:
<223> OTHER INFORMATION: Artificially synthesized antigenic peptide
      derived from FMNL1/KW13

```
<400> SEQUENCE: 24

Gln Ser Leu Asp Ala Leu Leu Glu Met
1               5

<210> SEQ ID NO 25
<211> LENGTH: 1100
<212> TYPE: PRT
<213> ORGANISM: Homo sapiens

<400> SEQUENCE: 25

Met Gly Asn Ala Ala Gly Ser Ala Glu Gln Pro Ala Gly Pro Ala Ala
1               5                   10                  15

Pro Pro Pro Lys Gln Pro Ala Pro Lys Gln Pro Met Pro Ala Ala
            20                  25                  30

Gly Glu Leu Glu Glu Arg Phe Asn Arg Ala Leu Asn Cys Met Asn Leu
        35                  40                  45

Pro Pro Asp Lys Val Gln Leu Leu Ser Gln Tyr Asp Asn Glu Lys Lys
    50                  55                  60

Trp Glu Leu Ile Cys Asp Gln Glu Arg Phe Gln Val Lys Asn Pro Pro
65                  70                  75                  80

Ala Ala Tyr Ile Gln Lys Leu Lys Ser Tyr Val Asp Thr Gly Gly Val
                85                  90                  95

Ser Arg Lys Val Ala Ala Asp Trp Met Ser Asn Leu Gly Phe Lys Arg
            100                 105                 110

Arg Val Gln Glu Ser Thr Gln Val Leu Arg Glu Leu Glu Thr Ser Leu
        115                 120                 125

Arg Thr Asn His Ile Gly Trp Val Gln Glu Phe Leu Asn Glu Glu Asn
    130                 135                 140

Arg Gly Leu Asp Val Leu Leu Glu Tyr Leu Ala Phe Ala Gln Cys Ser
145                 150                 155                 160

Val Thr Tyr Asp Met Glu Ser Thr Asp Asn Gly Ala Ser Asn Ser Glu
                165                 170                 175

Lys Asn Lys Pro Leu Glu Gln Ser Val Glu Asp Leu Ser Lys Gly Pro
            180                 185                 190

Pro Ser Ser Val Pro Lys Ser Arg His Leu Thr Ile Lys Leu Thr Pro
        195                 200                 205

Ala His Ser Arg Lys Ala Leu Arg Asn Ser Arg Ile Val Ser Gln Lys
    210                 215                 220

Asp Asp Val His Val Cys Ile Met Cys Leu Arg Ala Ile Met Asn Tyr
225                 230                 235                 240

Gln Ser Gly Phe Ser Leu Val Met Asn His Pro Ala Cys Val Asn Glu
                245                 250                 255

Ile Ala Leu Ser Leu Asn Asn Lys Asn Pro Arg Thr Lys Ala Leu Val
            260                 265                 270

Leu Glu Leu Leu Ala Ala Val Cys Leu Val Arg Gly Gly His Asp Ile
        275                 280                 285

Ile Leu Ala Ala Phe Asp Asn Phe Lys Glu Val Cys Gly Glu Gln His
    290                 295                 300

Arg Phe Glu Lys Leu Met Glu Tyr Phe Arg Asn Glu Asp Ser Asn Ile
305                 310                 315                 320

Asp Phe Met Val Ala Cys Met Gln Phe Ile Asn Ile Val Val His Ser
                325                 330                 335

Val Glu Asn Met Asn Phe Arg Val Phe Leu Gln Tyr Glu Phe Thr His
            340                 345                 350
```

-continued

```
Leu Gly Leu Asp Leu Tyr Leu Glu Arg Leu Arg Leu Thr Glu Ser Asp
        355                 360                 365
Lys Leu Gln Val Gln Ile Gln Ala Tyr Leu Asp Asn Ile Phe Asp Val
    370                 375                 380
Gly Ala Leu Leu Glu Asp Thr Glu Thr Lys Asn Ala Val Leu Glu His
385                 390                 395                 400
Met Glu Glu Leu Gln Glu Gln Val Ala Leu Leu Thr Glu Arg Leu Arg
                405                 410                 415
Asp Ala Glu Asn Glu Ser Met Ala Lys Ile Ala Glu Leu Glu Lys Gln
            420                 425                 430
Leu Ser Gln Ala Arg Lys Glu Leu Glu Thr Leu Arg Glu Arg Phe Ser
        435                 440                 445
Glu Ser Thr Ala Met Gly Pro Ser Arg Arg Pro Pro Glu Pro Glu Lys
    450                 455                 460
Ala Pro Pro Ala Ala Pro Thr Arg Pro Ser Ala Leu Glu Leu Lys Val
465                 470                 475                 480
Glu Glu Leu Glu Glu Lys Gly Leu Ile Arg Ile Leu Arg Gly Pro Gly
                485                 490                 495
Asp Ala Val Ser Ile Glu Ile Leu Pro Val Ala Val Ala Thr Pro Ser
            500                 505                 510
Gly Gly Asp Ala Pro Thr Pro Gly Val Pro Thr Gly Ser Pro Ser Pro
        515                 520                 525
Asp Leu Ala Pro Ala Ala Glu Pro Ala Pro Gly Ala Ala Pro Pro Pro
    530                 535                 540
Pro Pro Pro Leu Pro Gly Leu Pro Ser Pro Gln Glu Ala Pro Pro Ser
545                 550                 555                 560
Ala Pro Pro Gln Ala Pro Pro Leu Pro Gly Ser Pro Glu Pro Pro Pro
                565                 570                 575
Ala Pro Pro Leu Pro Gly Asp Leu Pro Pro Pro Pro Pro Pro Pro Pro
            580                 585                 590
Pro Pro Pro Gly Thr Asp Gly Pro Val Pro Pro Pro Pro Pro Pro Pro
        595                 600                 605
Pro Pro Pro Pro Gly Gly Pro Asp Ala Leu Gly Arg Arg Asp Ser
    610                 615                 620
Glu Leu Gly Pro Gly Val Lys Ala Lys Lys Pro Ile Gln Thr Lys Phe
625                 630                 635                 640
Arg Met Pro Leu Leu Asn Trp Val Ala Leu Lys Pro Ser Gln Ile Thr
                645                 650                 655
Gly Thr Val Phe Thr Glu Leu Asn Asp Glu Lys Val Leu Gln Glu Leu
            660                 665                 670
Asp Met Ser Asp Phe Glu Glu Gln Phe Lys Thr Lys Ser Gln Gly Pro
        675                 680                 685
Ser Leu Asp Leu Ser Ala Leu Lys Ser Lys Ala Ala Gln Lys Ala Pro
    690                 695                 700
Ser Lys Ala Thr Leu Ile Glu Ala Asn Arg Ala Lys Asn Leu Ala Ile
705                 710                 715                 720
Thr Leu Arg Lys Gly Asn Leu Gly Ala Glu Arg Ile Cys Gln Ala Ile
                725                 730                 735
Glu Ala Tyr Asp Leu Gln Ala Leu Gly Leu Asp Phe Leu Glu Leu Leu
            740                 745                 750
Met Arg Phe Leu Pro Thr Glu Tyr Glu Arg Ser Leu Ile Thr Arg Phe
        755                 760                 765
Glu Arg Glu Gln Arg Pro Met Glu Glu Leu Ser Glu Glu Asp Arg Phe
    770                 775                 780
```

```
Met Leu Cys Phe Ser Arg Ile Pro Arg Leu Pro Glu Arg Met Thr Thr
785                 790                 795                 800

Leu Thr Phe Leu Gly Asn Phe Pro Asp Thr Ala Gln Leu Leu Met Pro
                    805                 810                 815

Gln Leu Asn Ala Ile Ile Ala Ala Ser Met Ser Ile Lys Ser Ser Asp
                820                 825                 830

Lys Leu Arg Gln Ile Leu Glu Ile Val Leu Ala Phe Gly Asn Tyr Met
            835                 840                 845

Asn Ser Ser Lys Arg Gly Ala Ala Tyr Gly Phe Arg Leu Gln Ser Leu
        850                 855                 860

Asp Ala Leu Leu Glu Met Lys Ser Thr Asp Arg Lys Gln Thr Leu Leu
865                 870                 875                 880

His Tyr Leu Val Lys Val Ile Ala Glu Lys Tyr Pro Gln Leu Thr Gly
                885                 890                 895

Phe His Ser Asp Leu His Phe Leu Asp Lys Ala Gly Ser Val Ser Leu
                900                 905                 910

Asp Ser Val Leu Ala Asp Val Arg Ser Leu Gln Arg Gly Leu Glu Leu
            915                 920                 925

Thr Gln Arg Glu Phe Val Arg Gln Asp Asp Cys Met Val Leu Lys Glu
            930                 935                 940

Phe Leu Arg Ala Asn Ser Pro Thr Met Asp Lys Leu Leu Ala Asp Ser
945                 950                 955                 960

Lys Thr Ala Gln Glu Ala Phe Glu Ser Val Val Glu Tyr Phe Gly Glu
                965                 970                 975

Asn Pro Lys Thr Thr Ser Pro Gly Leu Phe Phe Ser Leu Phe Ser Arg
                980                 985                 990

Phe Ile Lys Ala Tyr Lys Lys Ala Glu Gln Glu Val Glu Gln Trp Lys
            995                 1000                1005

Lys Glu Ala Ala Ala Gln Glu Ala Gly Ala Asp Thr Pro Gly Lys
    1010            1015                1020

Gly Glu Pro Pro Ala Pro Lys Ser Pro Pro Lys Ala Arg Arg Pro
    1025            1030                1035

Gln Met Asp Leu Ile Ser Glu Leu Lys Arg Arg Gln Gln Lys Glu
    1040            1045                1050

Pro Leu Ile Tyr Glu Ser Asp Arg Asp Gly Ala Ile Glu Asp Ile
    1055            1060                1065

Ile Thr Val Ile Lys Thr Val Pro Phe Thr Ala Arg Thr Gly Lys
    1070            1075                1080

Arg Thr Ser Arg Leu Leu Cys Glu Ala Ser Leu Gly Glu Glu Met
    1085            1090                1095

Pro Leu
    1100
```